United States Patent
Corbin et al.

(10) Patent No.: US 7,169,978 B2
(45) Date of Patent: Jan. 30, 2007

(54) SOYBEAN VARIETY XB38E06

(75) Inventors: Thomas Charles Corbin, Monticello, IL (US); Jeffrey Allan Thompson, Edwardsville, IL (US)

(73) Assignee: Pioneer Hi-Bred International, Inc., Johnston, IA (US)

( * ) Notice: Subject to any disclaimer, the term of this patent is extended or adjusted under 35 U.S.C. 154(b) by 0 days.

(21) Appl. No.: 11/343,529

(22) Filed: Jan. 31, 2006

(65) Prior Publication Data

US 2006/0107366 A1 May 18, 2006

(51) Int. Cl.
*A01H 5/00* (2006.01)
*A01H 5/10* (2006.01)
*A01H 1/02* (2006.01)
*C12N 5/04* (2006.01)
*C12N 15/82* (2006.01)

(52) U.S. Cl. .............. 800/312; 800/260; 435/415
(58) Field of Classification Search ........... 800/312, 800/260, 300–302; 435/415
See application file for complete search history.

(56) References Cited

U.S. PATENT DOCUMENTS

| | | |
|---|---|---|
| 6,605,760 B1 | 8/2003 | Corbin |
| 6,605,762 B1 | 8/2003 | Streit |
| 6,610,910 B1 | 8/2003 | Streit et al. |
| 6,806,404 B1 | 10/2004 | Streit |
| 6,846,975 B1 | 1/2005 | Streit |
| 6,849,789 B1 | 2/2005 | Streit |
| 6,864,407 B1 | 3/2005 | Corbin |
| 6,989,474 B1 | 1/2006 | Steiger |
| 7,053,273 B2 * | 5/2006 | Schultze ............... 800/312 |

OTHER PUBLICATIONS

Plant Variety Protection Certificate No. 200100084 Soybean 93B86, issued May 8, 2001.
Plant Variety Protection Certificate No. 200100080 Soybean 94B73, issued May 8, 2001.
Plant Variety Protection Certificate No. 200200084 Soybean 93B68, issued Jun. 10, 2002.
Plant Variety Protection Certificate No. 200100073 Soybean 93B85, issued May 8, 2001.
Plant Variety Protection Certificate No. 200500081 Soybean 93M51, issued Jun. 23, 2005.
Plant Variety Protection Certificate No. 200300101 Soybean 93B80, issued Jun. 24, 2003.
Plant Variety Protection Certificate No. 200300102 Soybean 93M90, issued Jul. 18, 2003.
Plant Variety Protection Certificate No. 200400077 Soybean 93M92, issued Aug. 19, 2004.
Plant Variety Protection Certificate No. 200400076 Soybean 93M93, issued Aug. 19, 2004.
Plant Variety Protection Certificate No. 200200100 Soybean 94B13, issued May 2, 2002.
U.S. Appl. No. 10/768,447, filed Jan. 30, 2004, Paul Stephens.
U.S. Appl. No. 10/272,277, filed Oct. 15, 2002, Thompson et al.
U.S. Appl. No. 11/048,379, filed Jan. 31, 2005, Debra Steiger.
U.S. Appl. No. 11/048,357, filed Jan. 31, 2005, Thomas Corbin.

* cited by examiner

*Primary Examiner*—Elizabeth F. McElwain
(74) *Attorney, Agent, or Firm*—Pioneer Hi-Bred International, Inc.

(57) ABSTRACT

According to the invention, there is provided a novel soybean variety designated XB38E06. This invention thus relates to the seeds of soybean variety XB38E06, to the plants of soybean XB38E06 to plant parts of soybean variety XB38E06 and to methods for producing a soybean plant produced by crossing plants of the soybean variety XB38E06 with another soybean plant, using XB38E06 as either the male or the female parent.

20 Claims, No Drawings

SOYBEAN VARIETY XB38E06

FIELD OF INVENTION

This invention is in the field of soybean breeding, specifically relating to a soybean variety designated XB38E06.

BACKGROUND OF INVENTION

The present invention relates to a new and distinctive soybean variety, designated XB38E06 which has been the result of years of careful breeding and selection as part of a soybean breeding program. There are numerous steps in the development of any novel, desirable plant germplasm. Plant breeding begins with the analysis and definition of problems and weaknesses of the current germplasm, the establishment of program goals, and the definition of specific breeding objectives. The next step is selection of germplasm that possess the traits to meet the program goals. The goal is to combine in a single variety an improved combination of desirable traits from the parental germplasm. These important traits may include but are not limited to higher seed yield, resistance to diseases and insects, tolerance to drought and heat, and better agronomic qualities.

These processes, which lead to the final step of marketing and distribution, can take from six to twelve years from the time the first cross is made. Therefore, development of new varieties is a time-consuming process that requires precise forward planning, efficient use of resources, and a minimum of changes in direction.

Soybean (*Glycine max*), is an important and valuable field crop. Thus, a continuing goal of soybean breeders is to develop stable, high yielding soybean varieties that are agronomically sound. The reasons for this goal are to maximize the amount of grain produced on the land used and to supply food for both animals and humans. To accomplish this goal, the soybean breeder must select and develop soybean plants that have the traits that result in superior varieties.

Pioneer soybean research staff create over 500,000 potential new varieties each year. Of those new varieties, less than 50 and more commonly less than 25 are actually selected for commercial use.

The soybean is the world's leading source of vegetable oil and protein meal. The oil extracted from soybeans is used for cooking oil, margarine, and salad dressings. Soybean oil is composed of saturated, monounsaturated and polyunsaturated fatty acids. It has a typical composition of 11% palmitic, 4% stearic, 25% oleic, 50% linoleic and 9% linolenic fatty acid content ("Economic Implications of Modified Soybean Traits Summary Report", Iowa Soybean Promotion Board & American Soybean Association Special Report 92S, May 1990). Changes in fatty acid composition for improved oxidative stability and nutrition are also important traits. Industrial uses for processed soybean oil include ingredients for paints, plastics, fibers, detergents, cosmetics, and lubricants. Soybean oil may be split, inter-esterified, sulfurized, epoxidized, polymerized, ethoxylated, or cleaved. Designing and producing soybean oil derivatives with improved functionality, oliochemistry, is a rapidly growing field. The typical mixture of triglycerides is usually split and separated into pure fatty acids, which are then combined with petroleum-derived alcohols or acids, nitrogen, sulfonates, chlorine, or with fatty alcohols derived from fats and oils.

Soybean is also used as a food source for both animals and humans. Soybean is widely used as a source of protein for animal feeds for poultry, swine and cattle. During processing of whole soybeans, the fibrous hull is removed and the oil is extracted. The remaining soybean meal is a combination of carbohydrates and approximately 50% protein.

For human consumption soybean meal is made into soybean flour which is processed to protein concentrates used for meat extenders or specialty pet foods. Production of edible protein ingredients from soybean offers a healthy, less expensive replacement for animal protein in meats as well as dairy-type products.

SUMMARY OF INVENTION

According to the invention, there is provided a novel soybean variety, designated XB38E06. This invention thus relates to the seeds of soybean variety XB38E06, to the plants of soybean XB38E06, to plant parts of soybean variety XB38E06 and to methods for producing a soybean plant produced by crossing soybean variety XB38E06 with another soybean plant, using XB38E06 as either the male or the female parent. This invention also relates to methods for introgressing a transgenic or mutant trait into soybean variety XB38E06 and to the soybean plants and plant parts produced by those methods. This invention also relates to soybean varieties or breeding varieties and plant parts derived from soybean variety XB38E06, to methods for producing other soybean varieties or plant parts derived from soybean variety XB38E06 and to the soybean plants, varieties, and their parts derived from use of those methods. This invention further relates to soybean seeds, plants, and plant parts produced by crossing the soybean variety XB38E06 with another soybean variety.

Definitions

Certain definitions used in the specification are provided below. Also in the examples which follow, a number of terms are used. In order to provide a clear and consistent understanding of the specification and claims, including the scope to be given such terms, the following definitions are provided:

ALLELE. Any of one or more alternative forms of a genetic sequence. In a diploid cell or organism, the two alleles of a given sequence typically occupy corresponding loci on a pair of homologous chromosomes.

ALTER. The utilization of up-regulation, down-regulation, or gene silencing.

ANTHESIS. The time of a flower's opening.

BACKCROSSING. Process in which a breeder crosses a progeny variety back to one of the parental genotypes one or more times.

BREEDING. The genetic manipulation of living organisms.

BREEDING CROSS. A cross to introduce new genetic material into a plant for the development of a new variety. For example, one could cross plant A with plant B, wherein plant B would be genetically different from plant A. After the breeding cross, the resulting F1 plants could then be selfed or sibbed for one, two, three or more times (F1, F2, F3, etc.) until a new variety is developed. For clarification, such new variety would be within a pedigree distance of one breeding cross of plants A and B. The process described above would be referred to as one breeding cycle.

BU/A=Bushels per Acre. The seed yield in bushels/acre is the actual yield of the grain at harvest.

BSR=Brown Stem Rot Tolerance. This is a visual disease score from 1 to 9 comparing all genotypes in a given test. The score is based on leaf symptoms of yellowing and necrosis caused by brown stem rot. A score of 9 indicates no symptoms. Visual scores range down to a score of 1 which indicates severe symptoms of leaf yellowing and necrosis.

BSRLF=Brown Stem Rot disease rating based solely on leaf disease symptoms. This is a visual disease score from 1 to 9 comparing all genotypes in a given test. A score of 9 indicates no symptoms. Visual scores range down to a score of 1 which indicates severe symptoms.

BSRSTM=Brown Stem Rot disease rating based solely on stem disease symptoms. This is a visual disease score from 1 to 9 comparing all genotypes in a given test. A score of 9 indicates no symptoms. Visual scores range down to a score of 1 which indicates severe symptoms.

CELL. Cell as used herein includes a plant cell, whether isolated, in tissue culture or incorporated in a plant or plant part.

CW=Canopy Width. This is visual observation of the canopy width from 1 to 9 comparing all genotypes in a given test. The higher the score the better the canopy width observed.

CNKR=Stem Canker Tolerance. This is a visual disease score from 1 to 9 comparing all genotypes in a given test. The score is based upon premature plant death. A score of 9 indicates no symptoms, whereas a score of 1 indicates the entire experimental unit died very early.

COTYLEDON. A cotyledon is a type of seed leaf. The cotyledon contains the food storage tissues of the seed.

ELITE VARIETY. A variety that is sufficiently homozygous and homogeneous to be used for commercial grain production. An elite variety may also be used in further breeding.

EMBRYO. The embryo is the small plant contained within a mature seed.

EMGSC=Emergence Score. The percentage of emerged plants in a plot respective to the number of seeds planted.

F3. This symbol denotes a generation resulting from the selfing of the F2 generation along with selection for type and rogueing of off-types. The "F" number is a term commonly used in genetics, and designates the number of the filial generation. The "F3" generation denotes the offspring resulting from the selfing or self mating of members of the generation having the next lower "F" number, viz. the F2 generation.

FEC=Iron-deficiency Chlorosis. Plants are scored 1 to 9 based on visual observations. A score of 1 indicates the plants are dead or dying from iron-deficiency chlorosis, a score of 5 means plants have intermediate health with some leaf yellowing and a score of 9 means no stunting of the plants or yellowing of the leaves. Plots are usually scored in mid July.

FECL=Iron-deficiency Chlorosis. Plants are scored 1 to 9 based on visual observations. A score of 1 indicates the plants are dead or dying from iron-deficiency chlorosis, a score of 5 means plants have intermediate health with some leaf yellowing and a score of 9 means no stunting of the plants or yellowing of the leaves. Plots are scored around mid August.

FEY=Frogeye Tolerance. This is a visual disease score from 1 to 9 comparing all genotypes in a given test. The score is based upon leaf lesions. A score of 9 indicates no lesions, whereas a score of 1 indicates severe leaf necrosis.

GENE SILENCING. The interruption or suppression of the expression of a gene at the level of transcription or translation.

GENOTYPE. Refers to the genetic constitution of a cell or organism.

HABIT. This refers to the physical appearance of a plant. It can be determinate, semi-determinate, intermediate, or indeterminate. In soybeans, indeterminate varieties are those in which stem growth is not limited by formation of a reproductive structure (i.e., flowers, pods and seeds) and hence growth continues throughout flowering and during part of pod filling. The main stem will develop and set pods over a prolonged period under favorable conditions. In soybeans, determinate varieties are those in which stem growth ceases at flowering time. Most flowers develop simultaneously, and most pods fill at approximately the same time. The terms semi-determinate and intermediate are also used to describe plant habit and are defined in Bernard, R. L. 1972. "Two genes affecting stem termination in soybeans." Crop Science 12:235–239; Woodworth, C. M. 1932. "Genetics and breeding in the improvement of the soybean." Bull. Agric. Exp. Stn. (Illinois) 384:297–404; Woodworth, C. M. 1933. "Genetics of the soybean." J. Am. Soc. Agron. 25:36–51.

HERBRES=Herbicide Resistance. This indicates that the plant is more tolerant to the herbicide shown than the level of herbicide tolerance exhibited by wild type plants. A designation of RR indicates tolerance to glyphosate and a designation of STS indicates tolerance to sulfonylurea herbicides.

HGT=Plant Height. Plant height is taken from the top of the soil to top pod of the plant and is measured in inches.

HILUM. This refers to the scar left on the seed which marks the place where the seed was attached to the pod prior to it (the seed) being harvested.

HYPL=Hypocotyl Elongation. This score indicates the ability of the seed to emerge when planted 3" deep in sand pots and with a controlled temperature of 25° C. The number of plants that emerge each day are counted. Based on this data, each genotype is given a 1 to 9 score based on its rate of emergence and percent of emergence. A score of 9 indicates an excellent rate and percent of emergence, an intermediate score of 5 indicates average ratings and a 1 score indicates a very poor rate and percent of emergence.

HYPOCOTYL. A hypocotyl is the portion of an embryo or seedling between the cotyledons and the root. Therefore, it can be considered a transition zone between shoot and root.

LDGSEV=Lodging Resistance. Lodging is rated on a scale of 1 to 9. A score of 9 indicates erect plants. A score of 5 indicates plants are leaning at a 45° angle in relation to the ground and a score of 1 indicates plants are laying on the ground.

LEAFLETS. These are part of the plant shoot, and they manufacture food for the plant by the process of photosynthesis.

LINKAGE. Refers to a phenomenon wherein alleles on the same chromosome tend to segregate together more often than expected by chance if their transmission was independent.

LINKAGE DISEQUILIBRIUM. Refers to a phenomenon wherein alleles tend to remain together in linkage groups when segregating from parents to offspring, with a greater frequency than expected from their individual frequencies.

LLE=Linoleic Acid Percent. Linoleic acid is one of the five most abundant fatty acids in soybean seeds. It is measured by gas chromatography and is reported as a percent of the total oil content.

LLN=Linolenic Acid Percent. Linolenic acid is one of the five most abundant fatty acids in soybean seeds. It is measured by gas chromatography and is reported as a percent of the total oil content.

LOCUS. A defined segment of DNA.

MAT ABS=Absolute Maturity. This term is defined as the length of time from planting to complete physiological development (maturity). The period from planting until maturity is reached is measured in days, usually in comparison to one or more standard varieties. Plants are considered mature when 95% of the pods have reached their mature color.

MATURITY GROUP. This refers to an agreed-on industry division of groups of varieties, based on the zones in which they are adapted primarily according to day length or latitude. They consist of very long day length varieties (Groups 000, 00, 0), and extend to very short day length varieties (Groups VII, VIII, IX, X).

NEI DISTANCE. A quantitative measure of percent similarity between two lines. Nei's distance between lines A and B can be defined as 1−(2*number alleles in common/(number alleles in A+number alleles in B). For example, if lines A and B are the same for 95 out of 100 alleles, the Nei distance would be 0.05. If lines A and B are the same for 98 out of 100 alleles, the Nei distance would be 0.02. Free software for calculating Nei distance is available on the internet at multiple locations such as, for example, at: evolution.genetics.washington.edu/phylip.html. See Nei, Proc Natl Acad Sci, 76:5269–5273 (1979) which is incorporated by reference for this purpose.

OIL=Oil Percent. Soybean seeds contain a considerable amount of oil. Oil is measured by NIR spectrophotometry, and is reported on an as is percentage basis.

OLC=Oleic Acid Percent. Oleic acid is one of the five most abundant fatty acids in soybean seeds. It is measured by gas chromatography and is reported as a percent of the total oil content.

PEDIGREE DISTANCE. Relationship among generations based on their ancestral links as evidenced in pedigrees. May be measured by the distance of the pedigree from a given starting point in the ancestry.

PERCENT IDENTITY. Percent identity as used herein refers to the comparison of the homozygous alleles of two soybean varieties. Percent identity is determined by comparing a statistically significant number of the homozygous alleles of two developed varieties. For example, a percent identity of 90% between soybean variety 1 and soybean variety 2 means that the two varieties have the same allele at 90% of their loci.

PERCENT SIMILARITY. Percent similarity as used herein refers to the comparison of the homozygous alleles of a soybean variety such as XB38E06 with another plant, and if the homozygous allele of XB38E06 matches at least one of the alleles from the other plant then they are scored as similar. Percent similarity is determined by comparing a statistically significant number of loci and recording the number of loci with similar alleles as a percentage. A percent similarity of 90% between XB38E06 and another plant means that XB38E06 matches at least one of the alleles of the other plant at 90% of the loci.

PLANT. As used herein, the term "plant" includes reference to an immature or mature whole plant, including a plant from which seed or grain or anthers have been removed. Seed or embryo that will produce the plant is also considered to be the plant.

PLANT PARTS. As used herein, the term "plant parts" includes leaves, stems, roots, root tips, anthers, seed, grain, embryo, pollen, ovules, flowers, cotyledon, hypocotyl, pod, flower, shoot and stalk, tissue, cells and the like.

PLM=Palmitic Acid Percent. Palmitic acid is one of the five most abundant fatty acids in soybean seeds. It is measured by gas chromatography and is reported as a percent of the total oil content.

POD. This refers to the fruit of a soybean plant. It consists of the hull or shell (pericarp) and the soybean seeds.

PRT=*Phytophthora* Tolerance. Tolerance to *Phytophthora* root rot is rated on a scale of 1 to 9, with a score of 9 being the best or highest tolerance ranging down to a score of 1 which indicates the plants have no tolerance to *Phytophthora*.

PRMMAT=Predicted Relative Maturity. Soybean maturities are divided into relative maturity groups. In the United States the most common maturity groups are 00 through VIII. Within maturity groups 00 through V are sub-groups. A sub-group is a tenth of a relative maturity group. Within narrow comparisons, the difference of a tenth of a relative maturity group equates very roughly to a day difference in maturity at harvest.

PRO=Protein Percent. Soybean seeds contain a considerable amount of protein. Protein is generally measured by NIR spectrophotometry, and is reported on a dry weight basis.

PUBESCENCE. This refers to a covering of very fine hairs closely arranged on the leaves, stems and pods of the soybean plant.

R160=Palmitic Acid percentage—Percentage of palmitic acid as determined using methods described in Reske, et al., Triacylglycerol Composition and Structure in Genetically Modified Sunflower and Soybean Oils. JAOCS 74:8, 989–998 (1997), which is incorporated by reference for this purpose.

R180=Steric acid percentage—Percentage of Steric acid as determined using methods described in Reske, et al., Triacylglycerol Composition and Structure in Genetically Modified Sunflower and Soybean Oils. JAOCS 74:8, 989–998 (1997), which is incorporated by reference for this purpose.

R181=Oleic acid percentage—Percentage of oleic acid as determined using methods described in Reske, et al., Triacylglycerol Composition and Structure in Genetically Modified Sunflower and Soybean Oils. JAOCS 74:8, 989–998 (1997), which is incorporated by reference for this purpose.

R182=Linoleic acid percentage—Percentage of linoleic acid as determined using methods described in Reske, et al., Triacylglycerol Composition and Structure in Genetically Modified Sunflower and Soybean Oils. JAOCS 74:8, 989–998 (1997), which is incorporated by reference for this purpose.

R183=Linolenic acid percentage—Percentage of linolenic acid as determined using methods described in Reske, et al., Triacylglycerol Composition and Structure in Genetically Modified Sunflower and Soybean Oils. JAOCS 74:8, 989–998 (1997), which is incorporated by reference for this purpose.

RESISTANCE. Synonymous with tolerance. The ability of a plant to withstand exposure to an insect, disease, herbicide or other condition. A resistant plant variety will have a level of resistance higher than a comparable wild-type variety.

RKI=Root-knot Nematode, Southern. This is a visual disease score from 1 to 9 comparing all genotypes in a given test. The score is based upon digging plants to visually score the roots for presence or absence of galling. A score of 9 indicates that there is no galling of the roots, a score of 1 indicates large severe galling cover most of the root system which results in pre-mature death from decomposing of the root system.

RKA=Root-knot Nematode, Peanut. This is a visual disease score from 1 to 9 comparing all genotypes in a given test. The score is based upon digging plants to look at the roots for presence or absence of galling. A score of 9 indicates that there is no galling of the roots, a score of 1 indicates large severe galling cover most of the root system which results in pre-mature death from decomposing of the root system.

SCN=Soybean Cyst Nematode Resistance. The score is based on resistance to a particular race of soybean cyst nematode, such as race 1, 2, 3, 5 or 14. Scores are visual observations of resistance as versus other genotypes in the test, with a higher score indicating a higher level of resistance.

SD VIG=Seedling Vigor. The score is based on the speed of emergence of the plants within a plot relative to other plots within an experiment. A score of 9 indicates that 90% of plants growing have expanded first leaves. A score of 1 indicates no plants have expanded first leaves.

SDS=Sudden Death Syndrome. Tolerance to Sudden Death Syndrome is rated on a scale of 1 to 9, with a score of 1 being very susceptible ranging up to a score of 9 being tolerant.

SPLB or S/LB=Seeds per Pound. Soybean seeds vary in seed size, therefore, the number of seeds required to make up one pound also varies. This affects the pounds of seed required to plant a given area, and can also impact end uses.

SHATTR=Shattering. This refers to the amount of pod dehiscence prior to harvest. Pod dehiscence involves seeds falling from the pods to the soil. This is a visual score from 1 to 9 comparing all genotypes within a given test. A score of 9 means pods have not opened and no seeds have fallen out. A score of 5 indicates approximately 50% of the pods have opened, with seeds falling to the ground and a score of 1 indicates 100% of the pods are opened.

SHOOTS. These are a portion of the body of the plant. They consist of stems, petioles and leaves.

STC=Stearic Acid Percent. Stearic acid is one of the five most abundant fatty acids in soybean seeds. It is measured by gas chromatography and is reported as a percent of the total oil content.

WH MD=White Mold Tolerance. This is a visual disease score from 1 to 9 comparing all genotypes in a given test. The score is based upon observations of mycelial growth and death of plants. A score of 9 indicates no symptoms. Visual scores of 1 indicate complete death of the experimental unit.

Definitions for Area of Adaptability

When referring to area of adaptability, such term is used to describe the location with the environmental conditions that would be well suited for this soybean variety. Area of adaptability is based on a number of factors, for example: days to maturity, insect resistance, disease resistance, and drought resistance. Area of adaptability does not indicate that the soybean variety will grow in every location within the area of adaptability or that it will not grow outside the area. Area of adaptability may also be used to refer to the soil or growing conditions.

Midwest: Iowa and Missouri

Heartland: Illinois and the western half of Indiana

Plains: ⅔ of the eastern parts of South Dakota and Nebraska

North Central: Minnesota, Wisconsin, the Upper Peninsula of Michigan, and the eastern half of North Dakota Mideast: Michigan, Ohio, and the eastern half of Indiana Eastern: Pennsylvania, Delaware, Maryland, Rhode Island, New Jersey, Connecticut, Massachusetts, New York, Vermont, and Maine Southern: Virginia, West Virginia, Tennessee, Kentucky, Arkansas, North Carolina, South Carolina, Georgia, Florida, Alabama, Mississippi, and Louisiana Western: Texas, Kansas, Colorado, Oklahoma, New Mexico, Arizona, Utah, Nevada, California, Washington, Oregon, Montana, Idaho, Wyoming, the western half of North Dakota, and the western ⅓ South Dakota and Nebraska PMG infested soils: soils containing *Phytophthora sojae*

Narrow rows: 7" and 15" row spacing

High yield environments: areas which lack normal stress for example they have sufficient rainfall, water drainage, low disease pressure, and low weed pressure Tough environments: areas which have stress challenges, opposite of a high yield environment SCN infected soils: soils containing soybean cyst nematode other areas of adaptation include the soybean growing regions of Canada, tight clay soils, light sandy soils and no-till locations.

DETAILED DESCRIPTION OF INVENTION

The variety of the invention has shown uniformity and stability for all traits, as described in the following variety description information. It has been self-pollinated a sufficient number of generations, with careful attention to uniformity of plant type to ensure a sufficient level of homozygosity and phenotypic stability. The variety has been increased with continued observation for uniformity. No variant traits have been observed or are expected.

Soybean variety XB38E06 is particularly adapted to the Western, Midwest, Heartland, Mideast and Eastern regions of the United States. Strengths of soybean variety XB38E06 include good resistance to SCN Race 3, multi-race *Phytophthora* resistance (Rps1k), above average sudden death syndrome tolerance, very good frogeye leaf spot tolerance and resistance to labeled rates of Roundup branded herbicides.

Soybean variety XB38E06 demonstrates a valuable combination of traits. Few varieties at this RM have the yield potential, multi-race *phytophthora* resistance as governed by the Rps1-k gene, resistance to Race 3 of Soybean Cyst Nematode, resistance to Brown stem rot, resistance to Frogeye leaf spot, and resistance to Roundup branded herbicdes exhibited by XB38E06.

Soybean variety XB38E06 exhibits a relative maturity of 3 and a subgroup of approximately 8. A variety description of Soybean variety XB38E06 is provided in Table 1. Traits reported are average values for all locations and years or samples measured.

Soybean variety XB38E06, being substantially homozygous, can be reproduced by planting seeds of the variety, growing the resulting soybean plants under self-pollinating or sib-pollinating conditions, and harvesting the resulting seed, using techniques familiar to the agricultural arts.

Performance Examples of XB38E06

In the examples in Table 2, the traits and characteristics of soybean variety XB38E06 are given in paired comparisons with the Pioneer varieties shown in the following tables. Traits reported are mean values for all locations and years where paired comparison data was obtained.

FURTHER EMBODIMENTS OF THE INVENTION

Genetic Marker Profile Through SSR and First Generation Progeny

In addition to phenotypic observations, a plant can also be identified by its genotype. The genotype of a plant can be characterized through a genetic marker profile which can identify plants of the same variety or a related variety or be used to determine or validate a pedigree. Genetic marker profiles can be obtained by techniques such as Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length Polymorphisms (AFLPs), Simple Sequence Repeats (SSRs) which are also referred to as Microsatellites, and Single Nucleotide Polymorphisms (SNPs). For example, see Cregan et. al, "An Integrated Genetic Linkage Map of the Soybean Genome" Crop Science 39:1464–1490 (1999), and Berry et al., Assessing Probability of Ancestry Using Simple Sequence Repeat Profiles: Applications to Maize Inbred Lines and Soybean Varieties" Genetics 165:331–342 (2003), each of which are incorporated by reference herein in their entirety.

Particular markers used for these purposes are not limited to any particular set of markers, but are envisioned to include any type of marker and marker profile which provides a means of distinguishing varieties. One method of comparison is to use only homozygous loci for XB38E06. For example, one set of publicly available markers which could be used to screen and identify variety XB38E06 is disclosed in Table 3.

Primers and PCR protocols for assaying these and other markers are disclosed in the Soybase (sponsored by the USDA Agricultural Research Service and Iowa State University) located at the world wide web at 129.186.26.94/SSR.html. In addition to being used for identification of soybean variety XB38E06 and plant parts and plant cells of variety XB38E06, the genetic profile may be used to identify a soybean plant produced through the use of XB38E06 or to verify a pedigree for progeny plants produced through the use of XB38E06. The genetic marker profile is also useful in breeding and developing backcross conversions.

The present invention comprises a soybean plant characterized by molecular and physiological data obtained from the representative sample of said variety deposited with the ATCC. Further provided by the invention is a soybean plant formed by the combination of the disclosed soybean plant or plant cell with another soybean plant or cell and comprising the homozygous alleles of the variety.

Means of performing genetic marker profiles using SSR polymorphisms are well known in the art. SSRs are genetic markers based on polymorphisms in repeated nucleotide sequences, such as microsatellites. A marker system based on SSRs can be highly informative in linkage analysis relative to other marker systems in that multiple alleles may be present. Another advantage of this type of marker is that, through use of flanking primers, detection of SSRs can be achieved, for example, by the polymerase chain reaction (PCR), thereby eliminating the need for labor-intensive Southern hybridization. The PCR detection is done by use of two oligonucleotide primers flanking the polymorphic segment of repetitive DNA. Repeated cycles of heat denaturation of the DNA followed by annealing of the primers to their complementary sequences at low temperatures, and extension of the annealed primers with DNA polymerase, comprise the major part of the methodology.

Following amplification, markers can be scored by electrophoresis of the amplification products. Scoring of marker genotype is based on the size of the amplified fragment, which may be measured by the number of base pairs of the fragment. While variation in the primer used or in laboratory procedures can affect the reported fragment size, relative values should remain constant regardless of the specific primer or laboratory used. When comparing varieties it is preferable if all SSR profiles are performed in the same lab.

Primers used are publicly available and may be found in the Soybase or Cregan supra. See also, PCT Publication No. WO 99/31964 Nucleotide Polymorphisms in Soybean, U.S. Pat. No. 6,162,967 Positional Cloning of Soybean Cyst Nematode Resistance Genes, and US 2002/0129402A1 Soybean Sudden Death Syndrome Resistant Soybeans and Methods of Breeding and Identifying Resistant Plants, the disclosure of which are incorporated herein by reference.

The SSR profile of soybean plant XB38E06 can be used to identify plants comprising XB38E06 as a parent, since such plants will comprise the same homozygous alleles as XB38E06. Because the soybean variety is essentially homozygous at all relevant loci, most loci should have only one type of allele present. In contrast, a genetic marker profile of an F1 progeny should be the sum of those parents, e.g., if one parent was homozygous for allele x at a particular locus, and the other parent homozygous for allele y at that locus, then the F1 progeny will be xy (heterozygous) at that locus. Subsequent generations of progeny produced by selection and breeding are expected to be of genotype x (homozygous), y (homozygous), or xy (heterozygous) for that locus position. When the F1 plant is selfed or sibbed for successive filial generations, the locus should be either x or y for that position.

In addition, plants and plant parts substantially benefiting from the use of XB38E06 in their development, such as XB38E06 comprising a backcross conversion, transgene, or genetic sterility factor, may be identified by having a molecular marker profile with a high percent identity to XB38E06. Such a percent identity might be 95%, 96%, 97%, 98%, 99%, 99.5% or 99.9% identical to XB38E06.

The SSR profile of XB38E06 also can be used to identify essentially derived varieties and other progeny varieties developed from the use of XB38E06, as well as cells and other plant parts thereof. Such plants may be developed using the markers identified in WO 00/31964, U.S. Pat. No. 6,162,967 and US2002/0129402A1. Progeny plants and plant parts produced using XB38E06 may be identified by having a molecular marker profile of at least 25%, 30%, 35%, 40%, 45%, 50%, 55%, 60%, 65%, 70%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 99.5% genetic contribution from soybean variety, as measured by either percent identity or percent similarity. Such progeny may be further characterized as being within a pedigree distance of XB38E06, such as within 1, 2, 3, 4 or 5 or less cross-pollinations to a soybean plant other than XB38E06 or a plant that has XB38E06 as a progenitor. Unique molecular profiles may be identified with other molecular tools such as SNPs and RFLPs.

While determining the SSR genetic marker profile of the plants described supra, several unique SSR profiles may also be identified which did not appear in either parent of such plant. Such unique SSR profiles may arise during the breeding process from recombination or mutation. A combination of several unique alleles provides a means of identifying a plant variety, an F1 progeny produced from such variety, and progeny produced from such variety.

Introduction of a New Trait or Locus into XB38E06

Variety XB38E06 represents a new base genetic variety into which a new locus or trait may be introgressed. Direct transformation and backcrossing represent two important methods that can be used to accomplish such an introgression. The term backcross conversion and single locus conversion are used interchangeably to designate the product of a backcrossing program.

Backcross Conversions of XB38E06

A backcross conversion of XB38E06 occurs when DNA sequences are introduced through backcrossing (Hallauer et al, 1988), with XB38E06 utilized as the recurrent parent. Both naturally occurring and transgenic DNA sequences may be introduced through backcrossing techniques. A backcross conversion may produce a plant with a trait or locus conversion in at least two or more backcrosses, including at least 2 crosses, at least 3 crosses, at least 4 crosses, at least 5 crosses and the like. Molecular marker assisted breeding or selection may be utilized to reduce the number of backcrosses necessary to achieve the backcross conversion. For example, see Openshaw, S. J. et al., Marker-assisted Selection in Backcross Breeding. In: Proceedings Symposium of the Analysis of Molecular Data, August 1994, Crop Science Society of America, Corvallis, Oreg., where it is demonstrated that a backcross conversion can be made in as few as two backcrosses.

The complexity of the backcross conversion method depends on the type of trait being transferred (single genes or closely linked genes as vs. unlinked genes), the level of expression of the trait, the type of inheritance (cytoplasmic or nuclear) and the types of parents included in the cross. It is understood by those of ordinary skill in the art that for single gene traits that are relatively easy to classify, the backcross method is effective and relatively easy to manage. (See Hallauer et al. in Corn and Corn Improvement, Sprague and Dudley, Third Ed. 1998). Desired traits that may be transferred through backcross conversion include, but are not limited to, sterility (nuclear and cytoplasmic), fertility restoration, nutritional enhancements, drought tolerance, nitrogen utilization, altered fatty acid profile, low phytate, industrial enhancements, disease resistance (bacterial, fungal or viral), insect resistance and herbicide resistance. In addition, an introgression site itself, such as an FRT site, Lox site or other site specific integration site, may be inserted by backcrossing and utilized for direct insertion of one or more genes of interest into a specific plant variety. In some embodiments of the invention, the number of loci that may be backcrossed into XB38E06 is at least 1, 2, 3, 4, or 5 and/or no more than 6, 5, 4, 3, or 2. A single locus may contain several transgenes, such as a transgene for disease resistance that, in the same expression vector, also contains a transgene for herbicide resistance. The gene for herbicide resistance may be used as a selectable marker and/or as a phenotypic trait. A single locus conversion of site specific integration system allows for the integration of multiple genes at the converted loci.

The backcross conversion may result from either the transfer of a dominant allele or a recessive allele. Selection of progeny containing the trait of interest is accomplished by direct selection for a trait associated with a dominant allele. Transgenes transferred via backcrossing typically function as a dominant single gene trait and are relatively easy to classify. Selection of progeny for a trait that is transferred via a recessive allele requires growing and selfing the first backcross generation to determine which plants carry the recessive alleles. Recessive traits may require additional progeny testing in successive backcross generations to determine the presence of the locus of interest. The last backcross generation is usually selfed to give pure breeding progeny for the gene(s) being transferred, although a backcross conversion with a stably introgressed trait may also be maintained by further backcrossing to the recurrent parent with selection for the converted trait.

Along with selection for the trait of interest, progeny are selected for the phenotype of the recurrent parent. The backcross is a form of inbreeding, and the features of the recurrent parent are automatically recovered after successive backcrosses. Poehiman, Breeding Field Crops, P. 204 (1987). Poehiman suggests from one to four or more backcrosses, but as noted above, the number of backcrosses necessary can be reduced with the use of molecular markers. Other factors, such as a genetically similar donor parent, may also reduce the number of backcrosses necessary. As noted by Poehiman, backcrossing is easiest for simply inherited, dominant and easily recognized traits.

One process for adding or modifying a trait or locus in soybean variety XB38E06 comprises crossing XB38E06 plants grown from XB38E06 seed with plants of another soybean variety that comprise the desired trait or locus, selecting F1 progeny plants that comprise the desired trait or locus to produce selected F1 progeny plants, crossing the selected progeny plants with the XB38E06 plants to produce backcross progeny plants, selecting for backcross progeny plants that have the desired trait or locus and the morphological characteristics of soybean variety XB38E06 to produce selected backcross progeny plants; and backcrossing to XB38E06 three or more times in succession to produce selected fourth or higher backcross progeny plants that comprise said trait or locus. The modified XB38E06 may be further characterized as having the physiological and morphological characteristics of soybean variety XB38E06 listed in Table 1 as determined at the 5% significance level when grown in the same environmental conditions and/or may be characterized by percent similarity or identity to XB38E06 as determined by SSR markers. The above method may be utilized with fewer backcrosses in appropriate situations, such as when the donor parent is highly related or markers are used in the selection step. Desired traits that may be used include those nucleic acids known in the art, some of which are listed herein, that will affect traits through nucleic acid expression or inhibition. Desired loci include the introgression of FRT, Lox and other sites for site specific integration, which may also affect a desired trait if a functional nucleic acid is inserted at the integration site.

In addition, the above process and other similar processes described herein may be used to produce first generation progeny soybean seed by adding a step at the end of the process that comprises crossing XB38E06 with the introgressed trait or locus with a different soybean plant and harvesting the resultant first generation progeny soybean seed.

Transgenes

The advent of new molecular biological techniques has allowed the isolation and characterization of genetic elements with specific functions, such as encoding specific protein products. Scientists in the field of plant biology developed a strong interest in engineering the genome of plants to contain and express foreign genetic elements, or additional, or modified versions of native or endogenous genetic elements in order to alter the traits of a plant in a specific manner. Any DNA sequences, whether from a different species or from the same species, which are inserted into the genome using transformation are referred to herein collectively as "transgenes". In some embodiments of the invention, a transgenic variant of XB38E06 may contain at least one transgene but could contain at least 1, 2, 3, 4, 5, 6, 7, 8, 9, 10 and/or no more than 15, 14, 13, 12, 11, 10, 9, 8, 7, 6, 5, 4, 3, or 2. Over the last fifteen to twenty years several methods for producing transgenic plants have been developed, and the present invention also relates to transgenic variants of the claimed soybean variety XB38E06.

One embodiment of the invention is a process for producing soybean variety XB38E06 further comprising a desired trait, said process comprising transforming a soybean plant of variety XB38E06 with a transgene that confers a desired trait. Another embodiment is the product produced by this process. In one embodiment the desired trait may be one or more of herbicide resistance, insect resistance, disease resistance, decreased phytate, or modified fatty acid or carbohydrate metabolism. The specific gene may be any known in the art or listed herein, including; a polynucleotide conferring resistance to imidazolinone, sulfonylurea, glyphosate, glufosinate, triazine and benzonitrile; a polynucleotide encoding a *bacillus thuringiensis* polypeptide, a polynucleotide encoding phytase, FAD-2, FAD-3, galactinol synthase or a raffinose synthetic enzyme; or a polynucleotide conferring resistance to soybean cyst nematode, brown stem rot, *phytophthora* root rot, soybean mosaic virus or sudden death syndrome.

Numerous methods for plant transformation have been developed, including biological and physical plant transformation protocols. See, for example, Miki et al., "Procedures for Introducing Foreign DNA into Plants" in *Methods in Plant Molecular Biology and Biotechnology*, Glick, B. R. and Thompson, J. E. Eds. (CRC Press, Inc., Boca Raton, 1993) pages 67–88 and Armstrong, "The First Decade of Maize Transformation: A Review and Future Perspective" (Maydica 44:101–109, 1999). In addition, expression vectors and in vitro culture methods for plant cell or tissue transformation and regeneration of plants are available. See, for example, Gruber et al., "Vectors for Plant Transformation" in *Methods in Plant Molecular Biology and Biotechnology*, Glick, B. R. and Thompson, J. E. Eds. (CRC Press, Inc., Boca Raton, 1993) pages 89–119.

The most prevalent types of plant transformation involve the construction of an expression vector. Such a vector comprises a DNA sequence that contains a gene under the control of or operatively linked to a regulatory element, for example a promoter. The vector may contain one or more genes and one or more regulatory elements.

A genetic trait which has been engineered into the genome of a particular soybean plant may then be moved into the genome of another variety using traditional breeding techniques that are well known in the plant breeding arts. For example, a backcrossing approach is commonly used to move a transgene from a transformed soybean variety into an already developed soybean variety, and the resulting backcross conversion plant would then comprise the transgene(s).

Various genetic elements can be introduced into the plant genome using transformation. These elements include, but are not limited to genes; coding sequences; inducible, constitutive, and tissue specific promoters; enhancing sequences; and signal and targeting sequences. For example, see the traits, genes and transformation methods listed in U.S. Pat. No. 6,118,055.

With transgenic plants according to the present invention, a foreign protein can be produced in commercial quantities. Thus, techniques for the selection and propagation of transformed plants, which are well understood in the art, yield a plurality of transgenic plants that are harvested in a conventional manner, and a foreign protein then can be extracted from a tissue of interest or from total biomass. Protein extraction from plant biomass can be accomplished by known methods which are discussed, for example, by Heney and Orr, *Anal. Biochem.* 114: 92–6 (1981).

A genetic map can be generated, primarily via conventional Restriction Fragment Length Polymorphisms (RFLP), Polymerase Chain Reaction (PCR) analysis, Simple Sequence Repeats (SSR) and Single Nucleotide Polymorphisms (SNP) that identifies the approximate chromosomal location of the integrated DNA molecule. For exemplary methodologies in this regard, see Glick and Thompson, METHODS IN PLANT MOLECULAR BIOLOGY AND BIOTECHNOLOGY 269–284 (CRC Press, Boca Raton, 1993).

Wang et al. discuss "Large Scale Identification, Mapping and Genotyping of Single-Nucleotide Polymorphisms in the Human Genome", Science, 280:1077–1082, 1998, and similar capabilities are becoming increasingly available for the soybean genome. Map information concerning chromosomal location is useful for proprietary protection of a subject transgenic plant. If unauthorized propagation is undertaken and crosses made with other germplasm, the map of the integration region can be compared to similar maps for suspect plants to determine if the latter have a common parentage with the subject plant. Map comparisons would involve hybridizations, RFLP, PCR, SSR and sequencing, all of which are conventional techniques. SNPs may also be used alone or in combination with other techniques.

Likewise, by means of the present invention, plants can be genetically engineered to express various phenotypes of agronomic interest. Through the transformation of soybean the expression of genes can be altered to enhance disease resistance, insect resistance, herbicide resistance, agronomic, grain quality and other traits. Transformation can also be used to insert DNA sequences which control or help control male-sterility. DNA sequences native to soybean as well as non-native DNA sequences can be transformed into soybean and used to alter levels of native or non-native proteins. Various promoters, targeting sequences, enhancing sequences, and other DNA sequences can be inserted into the genome for the purpose of altering the expression of proteins. Reduction of the activity of specific genes (also known as gene silencing, or gene suppression) is desirable for several aspects of genetic engineering in plants.

Many techniques for gene silencing are well known to one of skill in the art, including but not limited to knock-outs (such as by insertion of a transposable element such as mu (Vicki Chandler, *The Maize Handbook* ch. 118 (Springer-Verlag 1994) or other genetic elements such as a FRT, Lox or other site specific integration site, antisense technology (see, e.g., Sheehy et al. (1988) *PNAS USA* 85:8805–8809; and U.S. Pat. Nos. 5,107,065; 5,453,566; and 5,759,829); co-suppression (e.g., Taylor (1997) *Plant Cell* 9:1245; Jorgensen (1990) *Trends Biotech.* 8(12):340–344; Flavell (1994) *PNAS USA* 91:3490–3496; Finnegan et al. (1994) *Bio/Technology* 12: 883–888; and Neuhuber et al. (1994) *Mol. Gen. Genet.* 244:230–241); RNA interference (Napoli et al. (1990) *Plant Cell* 2:279–289; U.S. Pat. No. 5,034,323; Sharp (1999) *Genes Dev.* 13:139–141; Zamore et al. (2000) *Cell* 101:25–33; and Montgomery et al. (1998) *PNAS USA*

95:15502–15507), virus-induced gene silencing (Burton, et al. (2000) *Plant Cell* 12:691–705; and Baulcombe (1999) *Curr. Op. Plant Bio.* 2:109–113); target-RNA-specific ribozymes (Haseloff et al. (1988) *Nature* 334: 585–591); hairpin structures (Smith et al. (2000) *Nature* 407:319–320; WO 99/53050; and WO 98/53083); MicroRNA (Aukerman & Sakai (2003) Plant Cell 15:2730–2741); ribozymes (Steinecke et al. (1992) *EMBO J.* 11:1525; and Perriman et al. (1993) *Antisense Res. Dev.* 3:253); oligonucleotide mediated targeted modification (e.g., WO 03/076574 and WO 99/25853); Zn-finger targeted molecules (e.g., WO 01/52620; WO 03/048345; and WO 00/42219); and other methods or combinations of the above methods known to those of skill in the art.

Exemplary nucleotide sequences that may be altered by genetic engineering include, but are not limited to, those categorized below.

1. Transgenes that Confer Resistance to Insects or Disease and That Encode:

(A) Plant disease resistance genes. Plant defenses are often activated by specific interaction between the product of a disease resistance gene (R) in the plant and the product of a corresponding avirulence (Avr) gene in the pathogen. A plant variety can be transformed with cloned resistance gene to engineer plants that are resistant to specific pathogen strains. See, for example Jones et al., Science 266: 789 (1994) (cloning of the tomato Cf-9 gene for resistance to *Cladosporium fulvum*); Martin et al., Science 262: 1432 (1993) (tomato Pto gene for resistance to *Pseudomonas syringae* pv. tomato encodes a protein kinase); Mindrinos et al., Cell 78: 1089 (1994) (*Arabidopsis* RSP2 gene for resistance to *Pseudomonas syringae*), McDowell & Woffenden, (2003) Trends Biotechnol. 21(4): 178–83 and Toyoda et al., (2002) Transgenic Res. 11 (6):567–82. A plant resistant to a disease is one that is more resistant to a pathogen as compared to the wild type plant.

(B) A *Bacillus thuringiensis* protein, a derivative thereof or a synthetic polypeptide modeled thereon. See, for example, Geiser et al., *Gene* 48: 109 (1986), who disclose the cloning and nucleotide sequence of a Bt delta-endotoxin gene. Moreover, DNA molecules encoding delta-endotoxin genes can be purchased from American Type Culture Collection (Rockville, Md.), for example, under ATCC Accession Nos. 40098, 67136, 31995 and 31998. Other examples of *Bacillus thuringiensis* transgenes being genetically engineered are given in the following patents and patent applications and hereby are incorporated by reference for this purpose: 5,188,960; 5,689,052; 5,880,275; WO 91/14778; WO 99/31248; WO 01/12731; WO 99/24581; WO 97/40162 and U.S. application Ser. Nos. 10/032,717; 10/414,637; and 10/606,320.

(C) An insect-specific hormone or pheromone such as an ecdysteroid and juvenile hormone, a variant thereof, a mimetic based thereon, or an antagonist or agonist thereof. See, for example, the disclosure by Hammock et al., Nature 344: 458 (1990), of baculovirus expression of cloned juvenile hormone esterase, an inactivator of juvenile hormone.

(D) An insect-specific peptide which, upon expression, disrupts the physiology of the affected pest. For example, see the disclosures of Regan, *J. Biol. Chem.* 269: 9 (1994) (expression cloning yields DNA coding for insect diuretic hormone receptor); Pratt et al., *Biochem. Biophys. Res. Comm.* 163: 1243 (1989) (an allostatin is identified in *Diploptera puntata*); Chattopadhyay et al. (2004) Critical Reviews in Microbiology 30 (1): 33–54 2004; Zjawiony (2004) J Nat Prod 67 (2): 300–310; Carlini & Grossi-de-Sa (2002) Toxicon, 40 (11): 1515–1539; Ussuf et al. (2001) Curr Sci. 80 (7): 847–853; and Vasconcelos & Oliveira (2004) Toxicon 44 (4): 385–403. See also U.S. Pat. No. 5,266,317 to Tomalski et al., who disclose genes encoding insect-specific toxins.

(E) An enzyme responsible for a hyperaccumulation of a monterpene, a sesquiterpene, a steroid, hydroxamic acid, a phenylpropanoid derivative or another non-protein molecule with insecticidal activity.

(F) An enzyme involved in the modification, including the post-translational modification, of a biologically active molecule; for example, a glycolytic enzyme, a proteolytic enzyme, a lipolytic enzyme, a nuclease, a cyclase, a transaminase, an esterase, a hydrolase, a phosphatase, a kinase, a phosphorylase, a polymerase, an elastase, a chitinase and a glucanase, whether natural or synthetic. See PCT application WO 93/02197 in the name of Scott et al., which discloses the nucleotide sequence of a callase gene. DNA molecules which contain chitinase-encoding sequences can be obtained, for example, from the ATCC under Accession Nos. 39637 and 67152. See also Kramer et al., *Insect Biochem. Molec. Biol.* 23: 691 (1993), who teach the nucleotide sequence of a cDNA encoding tobacco hookworm chitinase, and Kawalleck et al., *Plant Molec. Biol.* 21: 673 (1993), who provide the nucleotide sequence of the parsley ubi4-2 polyubiquitin gene, U.S. application Ser. Nos. 10/389,432, 10/692,367, and U.S. Pat. No. 6,563,020.

(G) A molecule that stimulates signal transduction. For example, see the disclosure by Botella et al., *Plant Molec. Biol.* 24: 757 (1994), of nucleotide sequences for mung bean calmodulin cDNA clones, and Griess et al., *Plant Physiol.* 104: 1467 (1994), who provide the nucleotide sequence of a maize calmodulin cDNA clone.

(H) A hydrophobic moment peptide. See PCT application WO 95/16776 and U.S. Pat. No. 5,580,852 disclosure of peptide derivatives of Tachyplesin which inhibit fungal plant pathogens) and PCT application WO 95/18855 and U.S. Pat. No. 5,607,914 (teaches synthetic antimicrobial peptides that confer disease resistance).

(I) A membrane permease, a channel former or a channel blocker. For example, see the disclosure by Jaynes et al., *Plant Sci.* 89: 43 (1993), of heterologous expression of a cecropin-beta lytic peptide analog to render transgenic tobacco plants resistant to *Pseudomonas solanacearum*.

(J) A viral-invasive protein or a complex toxin derived therefrom. For example, the accumulation of viral coat proteins in transformed plant cells imparts resistance to viral infection and/or disease development effected by the virus from which the coat protein gene is derived, as well as by related viruses. See Beachy et al., *Ann. Rev. Phytopathol.* 28: 451 (1990). Coat protein-mediated resistance has been conferred upon transformed plants against alfalfa mosaic virus, cucumber mosaic virus, tobacco streak virus, potato virus X, potato virus Y, tobacco etch virus, tobacco rattle virus and tobacco mosaic virus. Id.

(K) An insect-specific antibody or an immunotoxin derived therefrom. Thus, an antibody targeted to a critical metabolic function in the insect gut would inactivate an affected enzyme, killing the insect. Cf. Taylor et al., Abstract #497, SEVENTH INT'L SYMPOSIUM ON MOLECULAR PLANT-MICROBE INTERACTIONS (Edinburgh, Scotland, 1994) (enzymatic inactivation in transgenic tobacco via production of single-chain antibody fragments).

(L) A virus-specific antibody. See, for example, Tavladoraki et al., *Nature* 366: 469 (1993), who show that transgenic plants expressing recombinant antibody genes are protected from virus attack.

(M) A developmental-arrestive protein produced in nature by a pathogen or a parasite. Thus, fungal endo alpha-1,4-D-polygalacturonases facilitate fungal colonization and plant nutrient release by solubilizing plant cell wall homo-alpha-1,4-D-galacturonase. See Lamb et al., *Bio/Technology* 10: 1436 (1992). The cloning and characterization of a gene which encodes a bean endopolygalacturonase-inhibiting protein is described by Toubart et al., *Plant J.* 2: 367 (1992).

(N) A developmental-arrestive protein produced in nature by a plant. For example, Logemann et al., *Bio/Technology* 10: 305 (1992), have shown that transgenic plants expressing the barley ribosome-inactivating gene have an increased resistance to fungal disease.

(O) Genes involved in the Systemic Acquired Resistance (SAR) Response and/or the pathogenesis related genes. Briggs, S., Current Biology, 5(2) (1995), Pieterse & Van Loon (2004) Curr. Opin. Plant Bio. 7(4):456–64 and Somssich (2003) Cell 113(7):815–6.

(P) Antifungal genes (Cornelissen and Melchers, PI. Physiol. 101:709–712, (1993) and Parijs et al., Planta 183: 258–264, (1991) and Bushnell et al., Can. J. of Plant Path. 20(2):137–149 (1998). Also see U.S. application Ser. No. 09/950,933.

(Q) Detoxification genes, such as for fumonisin, beauvericin, moniliformin and zearalenone and their structurally related derivatives. For example, see U.S. Pat. No. 5,792,931.

(R) Cystatin and cysteine proteinase inhibitors. See U.S. application Ser. No. 10/947,979.

(S) Defensin genes. See WO03000863 and US application Ser. No. 10/178,213.

(T) Genes conferring resistance to nematodes, and in particular soybean cyst nematodes. See e.g. PCT Application WO96/30517; PCT Application WO93/19181, WO 03/033651 and Urwin et al., Planta 204:472–479 (1998), Williamson (1999) Curr Opin Plant Bio. 2(4):327–31.

(U) Genes that confer resistance to *Phytophthora* Root Rot, such as the Rps 1, Rps 1-a, Rps 1-b, Rps 1-c, Rps 1-d, Rps 1-e, Rps 1-k, Rps 2, Rps 3-a, Rps 3-b, Rps 3-c, Rps 4, Rps 5, Rps 6, Rps 7 and other Rps genes. See, for example, Shoemaker et al, *Phytophthora* Root Rot Resistance Gene Mapping in Soybean, Plant Genome IV Conference, San Diego, Calif. (1995).

(V) Genes that confer resistance to Brown Stem Rot, such as described in U.S. Pat. No. 5,689,035 and incorporated by reference for this purpose.

2. Transgenes that Confer Resistance to a Herbicide, for Example:

(A) A herbicide that inhibits the growing point or meristem, such as an imidazolinone or a sulfonylurea. Exemplary genes in this category code for mutant ALS and AHAS enzyme as described, for example, by Lee et al., *EMBO J.* 7: 1241 (1988), and Miki et al., *Theor. Appl. Genet.* 80: 449 (1990), respectively. See also, U.S. Pat. Nos. 5,605,011; 5,013,659; 5,141,870; 5,767,361; 5,731,180; 5,304,732; 4,761,373; 5,331,107; 5,928,937; and 5,378,824; and international publication WO 96/33270.

(B) Glyphosate (resistance imparted by mutant 5-enolpyruvl-3-phosphikimate synthase (EPSP) and aroA genes, respectively) and other phosphono compounds such as glufosinate (phosphinothricin acetyl transferase (PAT) and *Streptomyces hygroscopicus* phosphinothricin acetyl transferase (bar) genes), and pyridinoxy or phenoxy proprionic acids and cycloshexones (ACCase inhibitor-encoding genes). See, for example, U.S. Pat. No. 4,940,835 to Shah et al., which discloses the nucleotide sequence of a form of EPSPS which can confer glyphosate resistance. U.S. Pat. No. 5,627,061 to Barry et al. also describes genes encoding EPSPS enzymes. See also U.S. Pat. Nos. 6,566,587; 6,338,961; 6,248,876 B1; 6,040,497; 5,804,425; 5,633,435; 5,145,783; 4,971,908; 5,312,910; 5,188,642; 4,940,835; 5,866,775; 6,225,114 B1; 6,130,366; 5,310,667; 4,535,060; 4,769,061; 5,633,448; 5,510,471; Re. 36,449; RE 37,287 E; and 5,491,288; and international publications EP1173580; WO 01/66704; EP1173581 and EP1173582, which are incorporated herein by reference for this purpose. Glyphosate resistance is also imparted to plants that express a gene that encodes a glyphosate oxido-reductase enzyme as described more fully in U.S. Pat. Nos. 5,776,760 and 5,463,175, which are incorporated herein by reference for this purpose. In addition glyphosate resistance can be imparted to plants by the over expression of genes encoding glyphosate N-acetyltransferase. See, for example, U.S. application Ser. Nos. US01/46227; 10/427,692 and 10/427,692. A DNA molecule encoding a mutant aroA gene can be obtained under ATCC accession No. 39256, and the nucleotide sequence of the mutant gene is disclosed in U.S. Pat. No. 4,769,061 to Comai. European Patent Application No. 0 333 033 to Kumada et al. and U.S. Pat. No. 4,975,374 to Goodman et al. disclose nucleotide sequences of glutamine synthetase genes which confer resistance to herbicides such as L-phosphinothricin. The nucleotide sequence of a phosphinothricin-acetyl-transferase gene is provided in European Patent No. 0 242 246 and 0 242 236 to Leemans et al. De Greef et al., *Bio/Technology* 7: 61 (1989), describe the production of transgenic plants that express chimeric bar genes coding for phosphinothricin acetyl transferase activity. See also, U.S. Pat. Nos. 5,969,213; 5,489,520; 5,550,318; 5,874,265; 5,919,675; 5,561,236; 5,648,477; 5,646,024; 6,177,616 B1; and 5,879,903, which are incorporated herein by reference for this purpose. Exemplary genes conferring resistance to phenoxy proprionic acids and cycloshexones, such as sethoxydim and haloxyfop, are the Acc1-S1, Acc1-S2 and Acc1-S3 genes described by Marshall et al., *Theor. Appl. Genet.* 83: 435 (1992).

(C) A herbicide that inhibits photosynthesis, such as a triazine (psbA and gs+ genes) and a benzonitrile (nitrilase gene). Przibilla et al., *Plant Cell* 3: 169 (1991), describe the transformation of *Chlamydomonas* with plasmids encoding mutant psbA genes. Nucleotide sequences for nitrilase genes are disclosed in U.S. Pat. No. 4,810,648 to Stalker, and DNA molecules containing these genes are available under ATCC Accession Nos. 53435, 67441 and 67442. Cloning and expression of DNA coding for a glutathione S-transferase is described by Hayes et al., *Biochem. J.* 285: 173 (1992).

(D) Acetohydroxy acid synthase, which has been found to make plants that express this enzyme resistant to multiple types of herbicides, has been introduced into a variety of plants (see, e.g., Hattori et al. (1995) Mol Gen Genet 246:419). Other genes that confer resistance to herbicides include: a gene encoding a chimeric protein of rat cytochrome P4507A1 and yeast NADPH-cytochrome P450 oxidoreductase (Shiota et al. (1994) Plant Physiol 106:17), genes for glutathione reductase and superoxide dismutase (Aono et al. (1995) Plant Cell Physiol 36:1687, and genes for various phosphotransferases (Datta et al. (1992) Plant Mol Biol 20:619).

(E) Protoporphyrinogen oxidase (protox) is necessary for the production of chlorophyll, which is necessary for all plant survival. The protox enzyme serves as the target for a variety of herbicidal compounds. These herbicides also inhibit growth of all the different species of plants present, causing their total destruction. The development of plants containing altered protox activity which are resistant to these herbicides are described in U.S. Pat. Nos. 6,288,306 B1; 6,282,837 B1; and 5,767,373; and international publication WO 01/12825.

3. Transgenes that Confer or Contribute to an Altered Grain Characteristic, Such as:

(A) Altered fatty acids, for example, by
(1) Down-regulation of stearoyl-ACP desaturase to increase stearic acid content of the plant. See Knultzon et al., Proc. Natl. Acad. Sci. USA 89: 2624 (1992) and WO99/64579 (Genes for Desaturases to Alter Lipid Profiles in Corn),
(2) Elevating oleic acid via FAD-2 gene modification and/or decreasing linolenic acid via FAD-3 gene modification (see U.S. Pat. Nos. 6,063,947; 6,323,392; 6,372,965 and WO 93/11245),
(3) Altering conjugated linolenic or linoleic acid content, such as in WO 01/12800,
(4) Altering LEC1, AGP, Dek1, Superal1, milps, various Ipa genes such as Ipa1, Ipa3, hpt or hggt. For example, see WO 02/42424, WO 98/22604, WO 03/011015, U.S. Pat. Nos. 6,423,886, 6,197,561, 6,825,397, US2003/0079247, US2003/0204870, WO02/057439, WO03/011015 and Rivera-Madrid, R. et al. Proc. Natl. Acad. Sci. 92:5620–5624 (1995).

(B) Altered phosphorus content, for example, by the
(1) Introduction of a phytase-encoding gene would enhance breakdown of phytate, adding more free phosphate to the transformed plant. For example, see Van Hartingsveldt et al., Gene 127: 87 (1993), for a disclosure of the nucleotide sequence of an Aspergillus niger phytase gene.
(2) Up-regulation of a gene that reduces phytate content. In maize, this, for example, could be accomplished, by cloning and then re-introducing DNA associated with one or more of the alleles, such as the LPA alleles, identified in maize mutants characterized by low levels of phytic acid, such as in Raboy et al., Maydica 35: 383 (1990) and/or by altering inositol kinase activity as in WO 02/059324, US2003/0009011, WO 03/027243, US2003/0079247, WO 99/05298, U.S. Pat. Nos. 6197561, 6291224, 6391348, WO2002/059324, 2003/0079247, WO98/45448, WO99/55882, WO01/04147.

(C) Altered carbohydrates effected, for example, by altering a gene for an enzyme that affects the branching pattern of starch or, a gene altering thioredoxin such as NTR and/or TRX (see. (See U.S. Pat. No. 6,531,648 which is incorporated by reference for this purpose) and/or a gamma zein knock out or mutant such as cs27 or TUSC27 or en27 (See U.S. Pat. No. 6,858,778 and US2005/0160488, US2005/0204418; which are incorporated by reference for this purpose). See Shiroza et al., J. Bacteriol. 170: 810 (1988) (nucleotide sequence of Streptococcus mutans fructosyltransferase gene), Steinmetz et al., Mol. Gen. Genet. 200: 220 (1985) (nucleotide sequence of Bacillus subtilis levansucrase gene), Pen et al., Bio/Technology 10: 292 (1992) (production of transgenic plants that express Bacillus licheniformis alpha-amylase), Elliot et al., Plant Molec. Biol. 21: 515 (1993) (nucleotide sequences of tomato invertase genes), Søgaard et al., J. Biol. Chem. 268: 22480 (1993) (site-directed mutagenesis of barley alpha-amylase gene), and Fisher et al., Plant Physiol. 102: 1045 (1993) (maize endosperm starch branching enzyme II), WO 99/10498 (improved digestibility and/or starch extraction through modification of UDP-D-xylose 4-epimerase, Fragile 1 and 2, Refl, HCHL, C4H), U.S. Pat. No. 6,232,529 (method of producing high oil seed by modification of starch levels (AGP)). The fatty acid modification genes mentioned above may also be used to affect starch content and/or composition through the interrelationship of the starch and oil pathways.

(D) Altered antioxidant content or composition, such as alteration of tocopherol or tocotrienols. For example, see U.S. Pat. No. 6,787,683, US2004/0034886 and WO 00/68393 involving the manipulation of antioxidant levels through alteration of a phytl prenyl transferase (ppt), WO 03/082899 through alteration of a homogentisate geranyl geranyl transferase (hggt).

(E) Altered essential seed amino acids. For example, see U.S. Pat. No. 6,127,600 (method of increasing accumulation of essential amino acids in seeds), U.S. Pat. No. 6,080,913 (binary methods of increasing accumulation of essential amino acids in seeds), U.S. Pat. No. 5,990,389 (high lysine), WO99/40209 (alteration of amino acid compositions in seeds), WO99/29882 (methods for altering amino acid content of proteins), U.S. Pat. No. 5,850,016 (alteration of amino acid compositions in seeds), WO98/20133 (proteins with enhanced levels of essential amino acids), U.S. Pat. No. 5,885,802 (high methionine), U.S. Pat. No. 5,885,801 (high threonine), U.S. Pat. No. 6,664,445 (plant amino acid biosynthetic enzymes), U.S. Pat. No. 6,459,019 (increased lysine and threonine), U.S. Pat. No. 6,441,274 (plant tryptophan synthase beta subunit), U.S. Pat. No. 6,346,403 (methionine metabolic enzymes), U.S. Pat. No. 5,939,599 (high sulfur), U.S. Pat. No. 5,912,414 (increased methionine), WO98/56935 (plant amino acid biosynthetic enzymes), WO98/45458 (engineered seed protein having higher percentage of essential amino acids), WO98/42831 (increased lysine), U.S. Pat. No. 5,633,436 (increasing sulfur amino acid content), U.S. Pat. No. 5,559,223 (synthetic storage proteins with defined structure containing programmable levels of essential amino acids for improvement of the nutritional value of plants), WO96/01905 (increased threonine), WO95/15392 (increased lysine), US2003/0163838, US2003/0150014, US2004/0068767, U.S. Pat. No. 6,803,498, WO01/79516, and WO00/09706 (Ces A: cellulose synthase), U.S. Pat. No. 6,194,638 (hemicellulose), U.S. Pat. No. 6,399,859 and US2004/0025203 (UDPGdH), U.S. Pat. No. 6,194,638 (RGP).

4. Genes that Control Male-Sterility

There are several methods of conferring genetic male sterility available, such as multiple mutant genes at separate locations within the genome that confer male sterility, as disclosed in U.S. Pat. Nos. 4,654,465 and 4,727,219 to Brar et al. and chromosomal translocations as described by Patterson in U.S. Pat. Nos. 3,861,709 and 3,710,511. In addition to these methods, Albertsen et al., U.S. Pat. No. 5,432,068, describe a system of nuclear male sterility which includes: identifying a gene which is critical to male fertility; silencing this native gene which is critical to male fertility; removing the native promoter from the essential male fertility gene and replacing it with an inducible promoter; inserting this genetically engineered gene back into the plant; and thus creating a plant that is male sterile because the inducible promoter is not "on" resulting in the male fertility gene not being transcribed. Fertility is restored by inducing, or turning "on", the promoter, which in turn allows the gene that confers male fertility to be transcribed.

(A) Introduction of a deacetylase gene under the control of a tapetum-specific promoter and with the application of the chemical N-Ac-PPT (WO 01/29237).

(B) Introduction of various stamen-specific promoters (WO 92/13956, WO 92/13957).

(C) Introduction of the barnase and the barstar gene (Paul et al. Plant Mol. Biol. 19:611–622, 1992).

For additional examples of nuclear male and female sterility systems and genes, see also, U.S. Pat. Nos. 5,859,341; 6,297,426; 5,478,369; 5,824,524; 5,850,014; and 6,265,640; all of which are hereby incorporated by reference.

5. Genes that create a site for site specific DNA integration. This includes the introduction of FRT sites that may be used in the FLP/FRT system and/or Lox sites that may be used in the Cre/Loxp system. For example, see Lyznik, et al., Site-Specific Recombination for Genetic Engineering in Plants, Plant Cell Rep (2003) 21:925–932 and WO 99/25821, which are hereby incorporated by reference. Other systems that may be used include the Gin recombinase of phage Mu (Maeser et al., 1991; Vicki Chandler, *The Maize Handbook* ch. 118 (Springer-Verlag 1994), the Pin recombinase of *E. coli* (Enomoto et al., 1983), and the R/RS system of the pSR1 plasmid (Araki et al., 1992).

6. Genes that affect abiotic stress resistance (including but not limited to flowering, ear and seed development, enhancement of nitrogen utilization efficiency, altered nitrogen responsiveness, drought resistance or tolerance, cold resistance or tolerance, and salt resistance or tolerance) and increased yield under stress. For example, see: WO 00/73475 where water use efficiency is altered through alteration of malate; U.S. Pat. Nos. 5,892,009, 5,965,705, 5,929,305, 5,891,859, 6,417,428, 6,664,446, 6,706,866, 6,717,034, WO2000060089, WO2001026459, WO2001035725, WO2001034726, WO2001035727, WO2001036444, WO2001036597, WO2001036598, WO2002015675, WO2002017430, WO2002077185, WO2002079403, WO2003013227, WO2003013228, WO2003014327, WO2004031349, WO2004076638, WO9809521, and WO9938977 describing genes, including CBF genes and transcription factors effective in mitigating the negative effects of freezing, high salinity, and drought on plants, as well as conferring other positive effects on plant phenotype; US2004/0148654 and WO01/36596 where abscisic acid is altered in plants resulting in improved plant phenotype such as increased yield and/or increased tolerance to abiotic stress; WO2000/006341, WO04/090143, U.S. application Ser. Nos. 10/817,483 and 09/545,334 where cytokinin expression is modified resulting in plants with increased stress tolerance, such as drought tolerance, and/or increased yield. Also see WO0202776, WO2003052063, JP2002281975, U.S. Pat. No. 6,084,153, WO0164898, U.S. Pat. Nos. 6,177,275, and 6,107,547 (enhancement of nitrogen utilization and altered nitrogen responsiveness). For ethylene alteration, see US20040128719, US20030166197 and WO200032761. For plant transcription factors or transcriptional regulators of abiotic stress, see e.g. US20040098764 or US20040078852.

Other genes and transcription factors that affect plant growth and agronomic traits such as yield, flowering, plant growth and/or plant structure, can be introduced or introgressed into plants, see e.g. WO97/49811 (LHY), WO98/56918 (ESD4), WO97/10339 and U.S. Pat. No. 6573430 (TFL), U.S. Pat. No. 6713663 (FT), WO96/14414 (CON), WO96/38560, WO01/21822 (VRN1), WO00/44918 (VRN2), WO99/49064 (GI), WO00/46358 (FRI), WO97/29123, U.S. Pat. Nos.6794560, 6307126 (GAI), WO99/09174 (D8 and Rht), and WO2004076638 and WO2004031349 (transcription factors).

Using XB38E06 to Develop Other Soybean Varieties

Soybean varieties such as XB38E06 are typically developed for use in seed and grain production. However, soybean varieties such as XB38E06 also provide a source of breeding material that may be used to develop new soybean varieties. Plant breeding techniques known in the art and used in a soybean plant breeding program include, but are not limited to, recurrent selection, mass selection, bulk selection, mass selection, backcrossing, pedigree breeding, open pollination breeding, restriction fragment length polymorphism enhanced selection, genetic marker enhanced selection, making double haploids, and transformation. Often combinations of these techniques are used. The development of soybean varieties in a plant breeding program requires, in general, the development and evaluation of homozygous varieties. There are many analytical methods available to evaluate a new variety. The oldest and most traditional method of analysis is the observation of phenotypic traits but genotypic analysis may also be used.

Using XB38E06 in a Breeding Program

This invention is directed to methods for producing a soybean plant by crossing a first parent soybean plant with a second parent soybean plant wherein either the first or second parent soybean plant is variety XB38E06. The other parent may be any other soybean plant, such as a soybean plant that is part of a synthetic or natural population. Any such methods using soybean variety XB38E06 are part of this invention: selfing, sibbing, backcrosses, mass selection, pedigree breeding, bulk selection, hybrid production, crosses to populations, and the like. These methods are well known in the art and some of the more commonly used breeding methods are described below. Descriptions of breeding methods can be found in one of several reference books (e.g., Allard, *Principles of Plant Breeding*, 1960; Simmonds, *Principles of Crop Improvement*, 1979; Sneep et al., 1979; Fehr, "Breeding Methods for Cultivar Development", Chapter 7, *Soybean Improvement, Production and Uses*, $2^{nd}$ ed., Wilcox editor, 1987).

Pedigree Breeding

Pedigree breeding starts with the crossing of two genotypes, such as XB38E06 and another soybean variety having one or more desirable characteristics that is lacking or which complements XB38E06. If the two original parents do not provide all the desired characteristics, other sources can be included in the breeding population. In the pedigree method, superior plants are selfed and selected in successive filial generations. In the succeeding filial generations the heterozygous condition gives way to homogeneous varieties as a result of self-pollination and selection. Typically in the pedigree method of breeding, five or more successive filial generations of selfing and selection is practiced: $F1 \rightarrow F2$; $F2 \rightarrow F3$; $F3 \rightarrow F4$; $F4 \rightarrow F_5$, etc. After a sufficient amount of inbreeding, successive filial generations will serve to increase seed of the developed variety. Preferably, the developed variety comprises homozygous alleles at about 95% or more of its loci.

In addition to being used to create a backcross conversion, backcrossing can also be used in combination with pedigree breeding. As discussed previously, backcrossing can be used to transfer one or more specifically desirable traits from one variety, the donor parent, to a developed variety called the recurrent parent, which has overall good agronomic characteristics yet lacks that desirable trait or traits. However, the same procedure can be used to move the progeny toward the genotype of the recurrent parent but at the same time retain many components of the non-recurrent parent by stopping the backcrossing at an early stage and proceeding with selfing and selection. For example, a soybean variety may be crossed with another variety to produce a first generation progeny plant. The first generation progeny plant may then be backcrossed to one of its parent varieties to create a BC1 or BC2. Progeny are selfed and selected so that the newly developed variety has many of the attributes of the recurrent parent and yet several of the desired attributes of the non-recurrent parent. This approach leverages the value and strengths of the recurrent parent for use in new soybean varieties.

Therefore, an embodiment of this invention is a method of making a backcross conversion of soybean variety XB38E06, comprising the steps of crossing a plant of soybean variety XB38E06 with a donor plant comprising a desired trait, selecting an F1 progeny plant comprising the desired trait, and backcrossing the selected F1 progeny plant to a plant of soybean variety XB38E06. This method may further comprise the step of obtaining a molecular marker profile of soybean variety XB38E06 and using the molecular marker profile to select for a progeny plant with the desired trait and the molecular marker profile of XB38E06. In one embodiment the desired trait is a mutant gene or transgene present in the donor parent.

Recurrent Selection and Mass Selection

Recurrent selection is a method used in a plant breeding program to improve a population of plants. XB38E06 is suitable for use in a recurrent selection program. The method entails individual plants cross pollinating with each other to form progeny. The progeny are grown and the superior progeny selected by any number of selection methods, which include individual plant, half-sib progeny, full-sib progeny and selfed progeny. The selected progeny are cross pollinated with each other to form progeny for another population. This population is planted and again superior plants are selected to cross pollinate with each other. Recurrent selection is a cyclical process and therefore can be repeated as many times as desired. The objective of recurrent selection is to improve the traits of a population. The improved population can then be used as a source of breeding material to obtain new varieties for commercial or breeding use, including the production of a synthetic cultivar. A synthetic cultivar is the resultant progeny formed by the intercrossing of several selected varieties.

Mass selection is a useful technique when used in conjunction with molecular marker enhanced selection. In mass selection seeds from individuals are selected based on phenotype or genotype. These selected seeds are then bulked and used to grow the next generation. Bulk selection requires growing a population of plants in a bulk plot, allowing the plants to self-pollinate, harvesting the seed in bulk and then using a sample of the seed harvested in bulk to plant the next generation. Also, instead of self pollination, directed pollination could be used as part of the breeding program.

Mutation Breeding

Mutation breeding is another method of introducing new traits into soybean variety XB38E06. Mutations that occur spontaneously or are artificially induced can be useful sources of variability for a plant breeder. The goal of artificial mutagenesis is to increase the rate of mutation for a desired characteristic. Mutation rates can be increased by many different means including temperature, long-term seed storage, tissue culture conditions, radiation; such as X-rays, Gamma rays (e.g. cobalt 60 or cesium 137), neutrons, (product of nuclear fission by uranium 235 in an atomic reactor), Beta radiation (emitted from radioisotopes such as phosphorus 32 or carbon 14), or ultraviolet radiation (preferably from 2500 to 2900 nm), or chemical mutagens (such as base analogues (5-bromo-uracil), related compounds (8-ethoxy caffeine), antibiotics (streptonigrin), alkylating agents (sulfur mustards, nitrogen mustards, epoxides, ethylenamines, sulfates, sulfonates, sulfones, lactones), azide, hydroxylamine, nitrous acid, or acridines. Once a desired trait is observed through mutagenesis the trait may then be incorporated into existing germplasm by traditional breeding techniques. Details of mutation breeding can be found in "Principles of Cultivar Development" Fehr, 1993 Macmillan Publishing Company. In addition, mutations created in other soybean plants may be used to produce a backcross conversion of XB38E06 that comprises such mutation.

Breeding with Molecular Markers

Molecular markers, which includes markers identified through the use of techniques such as Isozyme Electrophoresis, Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length Polymorphisms (AFLPs), Simple Sequence Repeats (SSRs) and Single Nucleotide Polymorphisms (SNPs), may be used in plant breeding methods utilizing XB38E06.

Isozyme Electrophoresis and RFLPs have been widely used to determine genetic composition. Shoemaker and Olsen, ((1993) Molecular Linkage Map of Soybean (*Glycine max* L. Merr.). p. 6.131–6.138. In S. J. O'Brien (ed.) Genetic Maps: Locus Maps of Complex Genomes. Cold Spring Harbor Laboratory Press. Cold Spring Harbor, N.Y.), developed a molecular genetic linkage map that consisted of 25 linkage groups with about 365 RFLP, 11 RAPD (random amplified polymorphic DNA), three classical markers, and four isozyme loci. See also, Shoemaker R. C. 1994 RFLP Map of Soybean. P. 299–309 In R. L. Phillips and I. K. Vasil (ed.) DNA-based markers in plants. Kluwer Academic Press Dordrecht, the Netherlands.

SSR technology is currently the most efficient and practical marker technology; more marker loci can be routinely used and more alleles per marker locus can be found using SSRs in comparison to RFLPs. For example Diwan and Cregan, described a highly polymorphic microsatellite loci in soybean with as many as 26 alleles. (Diwan, N., and P. B. Cregan 1997 Automated sizing of fluorescent-labeled simple sequence repeat (SSR) markers to assay genetic variation in Soybean Theor. Appl. Genet. 95:220–225.) Single Nucleotide Polymorphisms may also be used to identify the unique genetic composition of the invention and progeny varieties retaining that unique genetic composition. Various molecular marker techniques may be used in combination to enhance overall resolution.

Soybean DNA molecular marker linkage maps have been rapidly constructed and widely implemented in genetic studies. One such study is described in Cregan et. al, "An Integrated Genetic Linkage Map of the Soybean Genome" Crop Science 39:1464–1490 (1999). Sequences and PCR conditions of SSR Loci in Soybean as well as the most current genetic map may be found in Soybase on the world wide web.

One use of molecular markers is Quantitative Trait Loci (QTL) mapping. QTL mapping is the use of markers, which are known to be closely linked to alleles that have measurable effects on a quantitative trait. Selection in the breeding process is based upon the accumulation of markers linked to the positive effecting alleles and/or the elimination of the markers linked to the negative effecting alleles from the plant's genome.

Molecular markers can also be used during the breeding process for the selection of qualitative traits. For example, markers closely linked to alleles or markers containing sequences within the actual alleles of interest can be used to select plants that contain the alleles of interest during a backcrossing breeding program. The markers can also be used to select for the genome of the recurrent parent and against the genome of the donor parent. Using this procedure can minimize the amount of genome from the donor parent that remains in the selected plants. It can also be used to reduce the number of crosses back to the recurrent parent needed in a backcrossing program. The use of molecular markers in the selection process is often called genetic marker enhanced selection.

Production of Double Haploids

The production of double haploids can also be used for the development of plants with a homozygous phenotype in the breeding program. For example, a soybean plant for which XB38E06 is a parent can be used to produce double haploid plants. Double haploids are produced by the doubling of a set of chromosomes (1N) from a heterozygous plant to produce a completely homozygous individual. For example, see Wan et al., "Efficient Production of Doubled Haploid Plants Through Colchicine Treatment of Anther-Derived Maize Callus", Theoretical and Applied Genetics, 77:889–892, 1989 and US2003/0005479. This can be advantageous because the process omits the generations of selfing needed to obtain a homozygous plant from a heterozygous source.

Haploid induction systems have been developed for various plants to produce haploid tissues, plants and seeds. The haploid induction system can produce haploid plants from any genotype by crossing a selected line (as female) with an inducer line. Such inducer lines for maize include Stock 6 (Coe, 1959, Am. Nat. 93:381–382; Sharkar and Coe, 1966, Genetics 54:453–464) RWS (see world wide web site www.uni-hohenheim.de/%7Eipspwww/350b/indexe.html#Project3), KEMS (Deimling, Roeber, and Geiger, 1997, Vortr. Pflanzenzuchtg 38:203–224), or KMS and ZMS (Chalyk, Bylich & Chebotar, 1994, MNL 68:47; Chalyk & Chebotar, 2000, Plant Breeding 119:363–364), and indeterminate gametophyte (ig) mutation (Kermicle 1969 Science 166:1422–1424). The disclosures of which are incorporated herein by reference.

Methods for obtaining haploid plants are also disclosed in Kobayashi, M. et al., Journ. of Heredity 71(1):9–14, 1980; Pollacsek, M., Agronomie (Paris) 12(3):247–251, 1992; Cho-Un-Haing et al., Journ. of Plant Biol., 1996, 39(3): 185–188; Verdoodt, L., et al., February 1998, 96(2):294–300; Genetic Manipulation in Plant Breeding, Proceedings International Symposium Organized by EUCARPIA, Sep. 8–13, 1985, Berlin, Germany; Chalyk et al., 1994, Maize Genet Coop. Newsletter 68:47; Chalyk, S.

Thus, an embodiment of this invention is a process for making a substantially homozygous XB38E06 progeny plant by producing or obtaining a seed from the cross of XB38E06 and another soybean plant and applying double haploid methods to the F1 seed or F1 plant or to any successive filial generation. Based on studies in maize and currently being conducted in soybean, such methods would decrease the number of generations required to produce a variety with similar genetics or characteristics to XB38E06. See Bernardo, R. and Kahler, A. L., Theor. Appl. Genet. 102:986–992, 2001.

In particular, a process of making seed retaining the molecular marker profile of soybean variety XB38E06 is contemplated, such process comprising obtaining or producing F1 seed for which soybean variety XB38E06 is a parent, inducing doubled haploids to create progeny without the occurrence of meiotic segregation, obtaining the molecular marker profile of soybean variety XB38E06, and selecting progeny that retain the molecular marker profile of XB38E06.

Use of XB38E06 in Tissue Culture

This invention is also directed to the use of variety XB38E06 in tissue culture. Tissue culture of various tissues of soybeans and regeneration of plants therefrom is well known and widely published. For example, reference may be had to Komatsuda, T. et al., "Genotype X Sucrose Interactions for Somatic Embryogenesis in Soybean," Crop Sci. 31:333–337 (1991); Stephens, P. A. et al., "Agronomic Evaluation of Tissue-Culture-Derived Soybean Plants," Theor. Appl. Genet. (1991) 82:633–635; Komatsuda, T. et al., "Maturation and Germination of Somatic Embryos as Affected by Sucrose and Plant Growth Regulators in Soybeans Glycine gracilis Skvortz and Glycine max (L.) Merr.," Plant Cell, Tissue and Organ Culture, 28:103–113 (1992); Dhir, S. et al., "Regeneration of Fertile Plants from Protoplasts of Soybean (Glycine max L. Merr.): Genotypic Differences in Culture Response," Plant Cell Reports (1992) 11:285–289; Pandey, P. et al., "Plant Regeneration from Leaf and Hypocotyl Explants of Glycine wightii (W. and A.) VERDC. var. longicauda," Japan J. Breed. 42:1–5 (1992); and Shetty, K., et al., "Stimulation of In Vitro Shoot Organogenesis in Glycine max (Merrill.) by Allantoin and Amides," Plant Science 81:(1992) 245–251; as well as U.S. Pat. No. 5,024,944, issued Jun. 18, 1991 to Collins et al. and U.S. Pat. No. 5,008,200, issued Apr. 16, 1991 to Ranch et al., the disclosures of which are hereby incorporated herein in their entirety by reference. Thus, another aspect of this invention is to provide cells which upon growth and differentiation produce soybean plants having the physiological and morphological characteristics of soybean variety XB38E06.

REFERENCES

Aukerman, M. J. et al. (2003) "Regulation of Flowering Time and Floral Organ Identity by a MicroRNA and Its APETALA2-like Target Genes" The Plant Cell 15:2730–2741

Berry et al., Assessing Probability of Ancestry Using Simple Sequence Repeat Profiles: Applications to Maize Inbred Lines and Soybean Varieties" Genetics 165:331–342 (2003)

Boppenmaier, et al., "Comparisons Among Strains of Inbreds for RFLPs", Maize Genetics Cooperative Newsletter, 65:1991, p. 90

Conger, B. V., et al. (1987) "Somatic Embryogenesis From Cultured Leaf Segments of Zea Mays", Plant Cell Reports, 6:345–347

Cregan et al, "An Integrated Genetic Linkage Map of the Soybean Genome" Crop Science 39:1464–1490 (1999).

Diwan et al., "Automated sizing of fluorescent-labeled simple sequence repeat (SSR) markers to assay genetic variation in Soybean" Theor. Appl. Genet. 95:220–225. (1997)

Duncan, D. R., et al. (1985) "The Production of Callus Capable of Plant Regeneration From Immature Embryos of Numerous Zea Mays Genotypes", Planta, 165:322–332

Edallo, et al. (1981) "Chromosomal Variation and Frequency of Spontaneous Mutation Associated with in Vitro Culture and Plant Regeneration in Maize", *Maydica*, XXVI:39–56

Fehr, Walt, Principles of Cultivar Development, pp. 261–286 (1987)

Green, et al. (1975) "Plant Regeneration From Tissue Cultures of Maize", *Crop Science*, Vol. 15, pp. 417–421

Green, C. E., et al. (1982) "Plant Regeneration in Tissue Cultures of Maize" *Maize for Biological Research*, pp. 367–372

Hallauer, A. R. et al. (1988) "Corn Breeding" *Corn and Corn Improvement*, No. 18, pp. 463–481

Lee, Michael (1994) "Inbred Lines of Maize and Their Molecular Markers", *The Maize Handbook*, Ch. 65:423–432

Meghji, M. R., et al. (1984) "Inbreeding Depression, Inbred & Hybrid Grain Yields, and Other Traits of Maize Genotypes Representing Three Eras", *Crop Science*, Vol. 24, pp. 545–549

Openshaw, S. J., et al. (1994) "Marker-assisted selection in backcross breeding". pp. 41–43. In Proceedings of the Symposium Analysis of Molecular Marker Data. 5–7 Aug. 1994. Corvallis, Oreg., American Society for Horticultural Science/Crop Science Society of America Phillips, et al. (1988) "Cell/Tissue Culture and In Vitro Manipulation", *Corn & Corn Improvement*, 3rd Ed., ASA Publication, No. 18, pp. 345–387

Poehlman et al (1995) *Breeding Field Crop*, 4th Ed., Iowa State University Press, Ames, Iowa, pp. 132–155 and 321–344

Rao, K. V., et al., (1986) "Somatic Embryogenesis in Glume Callus Cultures", *Maize Genetics Cooperative Newsletter*, No. 60, pp. 64–65

Sass, John F. (1977) "Morphology", *Corn & Corn Improvement*, ASA Publication, Madison, Wis. pp. 89–109

Smith, J. S. C., et al., "The Identification of Female Selfs in Hybrid Maize: A Comparison Using Electrophoresis and Morphology", Seed Science and Technology 14, 1–8

Songstad, D. D. et al. (1988) "Effect of ACC(1-aminocyclopropane-1-carboyclic acid), Silver Nitrate & Norbonadiene on Plant Regeneration From Maize Callus Cultures", *Plant Cell Reports*, 7:262–265

Tomes, et al. (1985) "The Effect of Parental Genotype on Initiation of Embryogenic Callus From Elite Maize (*Zea Mays* L.) Germplasm", *Theor. Appl. Genet.*, Vol. 70, p. 505–509

Troyer, et al. (1985) "Selection for Early Flowering in Corn: 10 Late Synthetics", *Crop Science*, Vol. 25, pp. 695–697

Umbeck, et al. (1983) "Reversion of Male-Sterile T-Cytoplasm Maize to Male Fertility in Tissue Culture", *Crop Science*, Vol. 23, pp. 584–588

Wan et al., "Efficient Production of Doubled Haploid Plants Through Colchicine Treatment of Anther-Derived Maize Callus", Theoretical and Applied Genetics, 77:889–892, 1989

Wright, Harold (1980) "Commercial Hybrid Seed Production", *Hybridization of Crop Plants*, Ch. 8:161–176

Wych, Robert D. (1988) "Production of Hybrid Seed", *Corn and Corn Improvement*, Ch. 9, pp. 565–607

DEPOSITS

Applicant(s) have made a deposit of at least 2500 seeds of Soybean Variety XB38E06 with the American Type Culture Collection (ATCC), Manassas, Va. 20110 USA, ATCC Deposit No. PTA-7743. The seeds to be deposited with the ATCC on Aug. 1, 2006 were taken from the deposit maintained by Pioneer Hi-Bred International, Inc., 7250 NW 62$^{nd}$ Avenue, Johnston, Iowa 50131 since prior to the filing date of this application. Access to this deposit will be available during the pendency of the application to the Commissioner of Patents and Trademarks and persons determined by the Commissioner to be entitled thereto upon request. Upon allowance of any claims in the application, the Applicant will make the deposit available to the public pursuant to 37 C.F.R. §1.808. This deposit of Soybean Variety XB38E06 will be maintained in the ATCC depository, which is a public depository, for a period of 30 years, or 5 years after the most recent request, or for the enforceable life of the patent, whichever is longer, and will be replaced if it becomes nonviable during that period. Additionally, Applicant has or will satisfy all the requirements of 37 C.F.R. §§1.801–1.809, including providing an indication of the viability of the sample upon deposit. Applicant has no authority to waive any restrictions imposed by law on the transfer of biological material or its transportation in commerce. Applicant does not waive any infringement of their rights granted under this patent or under the Plant Variety Protection Act (7 USC 2321 et seq.).

TABLE 1

| Variety Description Information for XB38E06 | |
|---|---|
| Traits | |
| Yield Potential | 9 |
| Relative Maturity | 38 |
| Canadian Heat Units | |
| Herbicide Resistance | RR |
| Harvest Standability | 6 |
| Field Emergence | 7 |
| Hypocotyl Length | 9 |
| Hypocotyl Length (Sales) | L |
| Phytophthora Gene | 1K |
| Phytophthora Race 4 | Resistant |
| Phytophthora Race 7 | Resistant |
| Phytophthora Race 25 | Susceptible |
| Phytophthora Field Tolerance | 5 |
| Brown Stem Rot | 9 |
| Iron Chlorosis | 3 |
| White Mold | |
| Sudden Death Syndrome | 6 |
| Cyst Nematode Race 1 | 1 |
| Cyst Nematode Race 2 | 3 |
| Cyst Nematode Race 3 | 7 |
| Cyst Nematode Race 5 | |
| Cyst Nematode Race 14 | |
| Root-knot Nematode - Southern | |
| Root-knot Nematode - Peanut | |
| Stem Canker | |
| Frogeye Leaf Spot | 8 |
| Aerial Web Blight | |
| Reduced Till Adaptability | 9 |
| Canopy Width | 6 |
| Shattering | |
| Height/Maturity | 8 |
| Plant Habit | Ind |
| Oil/Meal Type | |
| Seed Protein (% @ 13% H20) | 34.4 |
| Seed Oil (% @ 13% H20) | 19.2 |
| Seed Size (avg seeds/lb) | 3037 |
| Flower Color | White |
| Pubescence Color | Light Tawny |
| Hila Color | Black |
| Pod Color | Brown |
| Seed Coat Luster | Dull |

TABLE 2

VARIETY COMPARISON DATA

| Variety1 | Variety2 | Statistic | YIELD bu/a 60# ABS | MATABS count ABS | LDGSEV score ABS | HGT in ABS | FEC score ABS |
|---|---|---|---|---|---|---|---|
| XB38E06 | 93B68 | Mean1 | 58.5 | 132.8 | 6.8 | 40.6 | |
| XB38E06 | 93B68 | Mean2 | 53.5 | 131 | 7.9 | 38.9 | |
| XB38E06 | 93B68 | #Locs | 26 | 10 | 6 | 8 | |
| XB38E06 | 93B68 | #Reps | 54 | 19 | 9 | 14 | |
| XB38E06 | 93B68 | #Years | 1 | 1 | 1 | 1 | |
| XB38E06 | 93B68 | Diff | 5 | 1.8 | 1.1 | 1.7 | |
| XB38E06 | 93B68 | SE Diff | 1.06 | 0.67 | 0.44 | 0.6 | |
| XB38E06 | 93B68 | Prob | 0.0001 | 0.0252 | 0.0556 | 0.0256 | |
| XB38E06 | 93B85 | Mean1 | 58.1 | 131.8 | 6.4 | 40.3 | 3.2 |
| XB38E06 | 93B85 | Mean2 | 55 | 130.7 | 7.5 | 40.3 | 3.2 |
| XB38E06 | 93B85 | #Locs | 46 | 17 | 12 | 16 | 3 |
| XB38E06 | 93B85 | #Reps | 79 | 26 | 15 | 23 | 12 |
| XB38E06 | 93B85 | #Years | 2 | 2 | 2 | 2 | 1 |
| XB38E06 | 93B85 | Diff | 3.1 | 1.1 | 1.1 | 0.1 | 0 |
| XB38E06 | 93B85 | SE Diff | 0.82 | 0.76 | 0.28 | 0.66 | 0.14 |
| XB38E06 | 93B85 | Prob | 0.0004 | 0.1844 | 0.0027 | 0.9261 | 1 |
| XB38E06 | 93M51 | Mean1 | 58.1 | 131.8 | 6.4 | 40.3 | |
| XB38E06 | 93M51 | Mean2 | 55.8 | 127.7 | 6.9 | 39.5 | |
| XB38E06 | 93M51 | #Locs | 46 | 17 | 12 | 16 | |
| XB38E06 | 93M51 | #Reps | 78 | 26 | 15 | 23 | |
| XB38E06 | 93M51 | #Years | 2 | 2 | 2 | 2 | |
| XB38E06 | 93M51 | Diff | 2.4 | 4.1 | 0.5 | 0.8 | |
| XB38E06 | 93M51 | SE Diff | 0.85 | 0.67 | 0.18 | 0.6 | |
| XB38E06 | 93M51 | Prob | 0.0079 | 0 | 0.0204 | 0.1823 | |
| XB38E06 | 93M80 | Mean1 | 58.3 | 131.8 | 6.4 | 40.3 | 3.2 |
| XB38E06 | 93M80 | Mean2 | 56.2 | 132.6 | 7.3 | 43.6 | 3.2 |
| XB38E06 | 93M80 | #Locs | 45 | 17 | 12 | 16 | 3 |
| XB38E06 | 93M80 | #Reps | 76 | 26 | 15 | 23 | 12 |
| XB38E06 | 93M80 | #Years | 2 | 2 | 2 | 2 | 1 |
| XB38E06 | 93M80 | Diff | 2 | 0.8 | 0.9 | 3.3 | 0 |
| XB38E06 | 93M80 | SE Diff | 0.75 | 0.65 | 0.28 | 0.49 | 0 |
| XB38E06 | 93M80 | Prob | 0.01 | 0.2244 | 0.0089 | 0 | 1 |
| XB38E06 | 93M90 | Mean1 | 58.1 | 131.8 | 6.4 | 40.3 | 3.2 |
| XB38E06 | 93M90 | Mean2 | 55.8 | 132.9 | 8 | 42.7 | 2.2 |
| XB38E06 | 93M90 | #Locs | 46 | 17 | 12 | 16 | 3 |
| XB38E06 | 93M90 | #Reps | 79 | 26 | 15 | 23 | 12 |
| XB38E06 | 93M90 | #Years | 2 | 2 | 2 | 2 | 1 |
| XB38E06 | 93M90 | Diff | 2.3 | 1.1 | 1.5 | 2.4 | 1 |
| XB38E06 | 93M90 | SE Diff | 0.81 | 0.66 | 0.37 | 0.52 | 0.14 |
| XB38E06 | 93M90 | Prob | 0.0069 | 0.1095 | 0.0015 | 0.0004 | 0.0202 |
| XB38E06 | 93M92 | Mean1 | 58.5 | 132.8 | 6.8 | 40.6 | 3.2 |
| XB38E06 | 93M92 | Mean2 | 54.6 | 134.3 | 7.2 | 40.2 | 4.1 |
| XB38E06 | 93M92 | #Locs | 26 | 10 | 6 | 8 | 3 |
| XB38E06 | 93M92 | #Reps | 54 | 19 | 9 | 14 | 12 |
| XB38E06 | 93M92 | #Years | 1 | 1 | 1 | 1 | 1 |
| XB38E06 | 93M92 | Diff | 4 | 1.5 | 0.3 | 0.4 | 0.9 |
| XB38E06 | 93M92 | SE Diff | 1.46 | 0.76 | 0.31 | 0.73 | 0.51 |
| XB38E06 | 93M92 | Prob | 0.0118 | 0.0811 | 0.3276 | 0.5671 | 0.2123 |
| XB38E06 | 93M93 | Mean1 | 58.5 | 132.8 | 6.8 | 40.6 | 3.2 |
| XB38E06 | 93M93 | Mean2 | 56.3 | 135.8 | 8 | 44.1 | 4.3 |
| XB38E06 | 93M93 | #Locs | 26 | 10 | 6 | 8 | 3 |
| XB38E06 | 93M93 | #Reps | 55 | 19 | 9 | 14 | 12 |
| XB38E06 | 93M93 | #Years | 1 | 1 | 1 | 1 | 1 |
| XB38E06 | 93M93 | Diff | 2.3 | 3 | 1.2 | 3.5 | 1.1 |
| XB38E06 | 93M93 | SE Diff | 1.06 | 0.65 | 0.31 | 0.81 | 0.33 |
| XB38E06 | 93M93 | Prob | 0.0412 | 0.0012 | 0.0127 | 0.0034 | 0.0831 |
| XB38E06 | 94B13 | Mean1 | 58.5 | 132.8 | 6.8 | 40.6 | 3.2 |
| XB38E06 | 94B13 | Mean2 | 55.1 | 137.8 | 8 | 42.4 | 2.4 |
| XB38E06 | 94B13 | #Locs | 26 | 10 | 6 | 8 | 3 |
| XB38E06 | 94B13 | #Reps | 53 | 19 | 9 | 14 | 12 |
| XB38E06 | 94B13 | #Years | 1 | 1 | 1 | 1 | 1 |
| XB38E06 | 94B13 | Diff | 3.4 | 4.9 | 1.2 | 1.8 | 0.8 |
| XB38E06 | 94B13 | SE Diff | 1.28 | 1 | 0.38 | 0.63 | 0.29 |
| XB38E06 | 94B13 | Prob | 0.014 | 0.0008 | 0.0278 | 0.0243 | 0.1217 |
| XB38E06 | 93M81 | Mean1 | 58.5 | 132.8 | 6.8 | 40.6 | |
| XB38E06 | 93M81 | Mean2 | 56.2 | 134.1 | 8.5 | 39.9 | |
| XB38E06 | 93M81 | #Locs | 26 | 10 | 6 | 8 | |
| XB38E06 | 93M81 | #Reps | 54 | 19 | 9 | 14 | |
| XB38E06 | 93M81 | #Years | 1 | 1 | 1 | 1 | |
| XB38E06 | 93M81 | Diff | 2.4 | 1.3 | 1.7 | 0.8 | |
| XB38E06 | 93M81 | SE Diff | 1.12 | 0.92 | 0.36 | 0.63 | |
| XB38E06 | 93M81 | Prob | 0.0448 | 0.1911 | 0.0055 | 0.2753 | |
| XB38E06 | 93M82 | Mean1 | 58.5 | 132.8 | 6.8 | 40.6 | 3.2 |

TABLE 2-continued

VARIETY COMPARISON DATA

| Variety1 | Variety2 | Statistic | | | | | |
|---|---|---|---|---|---|---|---|
| XB38E06 | 93M82 | Mean2 | 58.7 | 134.7 | 7.3 | 43.1 | 4.5 |
| XB38E06 | 93M82 | #Locs | 26 | 10 | 6 | 8 | 3 |
| XB38E06 | 93M82 | #Reps | 55 | 19 | 9 | 14 | 12 |
| XB38E06 | 93M82 | #Years | 1 | 1 | 1 | 1 | 1 |
| XB38E06 | 93M82 | Diff | 0.2 | 1.8 | 0.4 | 2.5 | 1.3 |
| XB38E06 | 93M82 | SE Diff | 0.77 | 0.62 | 0.37 | 0.93 | 0.17 |
| XB38E06 | 93M82 | Prob | 0.8409 | 0.0158 | 0.3165 | 0.0306 | 0.0153 |

| Variety1 | Variety2 | Statistic | SDS score ABS | PRTLAB score ABS | EMGSC score ABS | SDVIG score ABS |
|---|---|---|---|---|---|---|
| XB38E06 | 93B68 | Mean1 | 8.2 | 5.3 | 6.7 | |
| XB38E06 | 93B68 | Mean2 | 7 | 5.7 | 7 | |
| XB38E06 | 93B68 | #Locs | 5 | 1 | 1 | |
| XB38E06 | 93B68 | #Reps | 9 | 3 | 3 | |
| XB38E06 | 93B68 | #Years | 1 | 1 | 1 | |
| XB38E06 | 93B68 | Diff | 1.2 | 0.3 | 0.3 | |
| XB38E06 | 93B68 | SE Diff | 0.51 | | | |
| XB38E06 | 93B68 | Prob | 0.0845 | | | |
| XB38E06 | 93B85 | Mean1 | 7.8 | 5.7 | 6.8 | 3 |
| XB38E06 | 93B85 | Mean2 | 7.3 | 6.4 | 7.7 | 4 |
| XB38E06 | 93B85 | #Locs | 7 | 2 | 2 | 1 |
| XB38E06 | 93B85 | #Reps | 12 | 5 | 4 | 1 |
| XB38E06 | 93B85 | #Years | 2 | 2 | 2 | 1 |
| XB38E06 | 93B85 | Diff | 0.5 | 0.8 | 0.8 | 1 |
| XB38E06 | 93B85 | SE Diff | 0.68 | 0.75 | 1.17 | |
| XB38E06 | 93B85 | Prob | 0.529 | 0.5 | 0.6051 | |
| XB38E06 | 93M51 | Mean1 | 7.8 | 5.7 | 6.8 | 3 |
| XB38E06 | 93M51 | Mean2 | 6.9 | 5.8 | 8.3 | 6 |
| XB38E06 | 93M51 | #Locs | 7 | 2 | 2 | 1 |
| XB38E06 | 93M51 | #Reps | 12 | 5 | 4 | 1 |
| XB38E06 | 93M51 | #Years | 2 | 2 | 2 | 1 |
| XB38E06 | 93M51 | Diff | 0.9 | 0.2 | 1.5 | 3 |
| XB38E06 | 93M51 | SE Diff | 0.42 | 0.17 | 0.5 | |
| XB38E06 | 93M51 | Prob | 0.0865 | 0.5 | 0.2048 | |
| XB38E06 | 93M80 | Mean1 | 7.8 | 5.7 | 6.8 | 3 |
| XB38E06 | 93M80 | Mean2 | 7.2 | 5.3 | 7.3 | 3 |
| XB38E06 | 93M80 | #Locs | 7 | 2 | 2 | 1 |
| XB38E06 | 93M80 | #Reps | 12 | 5 | 4 | 1 |
| XB38E06 | 93M80 | #Years | 2 | 2 | 2 | 1 |
| XB38E06 | 93M80 | Diff | 0.6 | 0.4 | 0.5 | 0 |
| XB38E06 | 93M80 | SE Diff | 0.6 | 0.92 | 1.5 | |
| XB38E06 | 93M80 | Prob | 0.3391 | 0.7284 | 0.7952 | |
| XB38E06 | 93M90 | Mean1 | 7.8 | 5.7 | 6.8 | 3 |
| XB38E06 | 93M90 | Mean2 | 7.6 | 5.1 | 7 | 5 |
| XB38E06 | 93M90 | #Locs | 7 | 2 | 2 | 1 |
| XB38E06 | 93M90 | #Reps | 12 | 5 | 4 | 1 |
| XB38E06 | 93M90 | #Years | 2 | 2 | 2 | 1 |
| XB38E06 | 93M90 | Diff | 0.2 | 0.6 | 0.2 | 2 |
| XB38E06 | 93M90 | SE Diff | 0.68 | 0.08 | 0.17 | |
| XB38E06 | 93M90 | Prob | 0.8134 | 0.0903 | 0.5 | |
| XB38E06 | 93M92 | Mean1 | 8.2 | 5.3 | 6.7 | |
| XB38E06 | 93M92 | Mean2 | 6.1 | 3.7 | 6.7 | |
| XB38E06 | 93M92 | #Locs | 5 | 1 | 1 | |
| XB38E06 | 93M92 | #Reps | 9 | 3 | 3 | |
| XB38E06 | 93M92 | #Years | 1 | 1 | 1 | |
| XB38E06 | 93M92 | Diff | 2.1 | 1.7 | 0 | |
| XB38E06 | 93M92 | SE Diff | 0.33 | | | |
| XB38E06 | 93M92 | Prob | 0.0032 | | | |
| XB38E06 | 93M93 | Mean1 | 8.2 | 5.3 | 6.7 | |
| XB38E06 | 93M93 | Mean2 | 7.7 | 4.7 | 7 | |
| XB38E06 | 93M93 | #Locs | 5 | 1 | 1 | |
| XB38E06 | 93M93 | #Reps | 9 | 3 | 3 | |
| XB38E06 | 93M93 | #Years | 1 | 1 | 1 | |
| XB38E06 | 93M93 | Diff | 0.5 | 0.7 | 0.3 | |
| XB38E06 | 93M93 | SE Diff | 0.47 | | | |
| XB38E06 | 93M93 | Prob | 0.3739 | | | |
| XB38E06 | 94B13 | Mean1 | 8.2 | 5.3 | 6.7 | |
| XB38E06 | 94B13 | Mean2 | 8 | 5 | 6 | |
| XB38E06 | 94B13 | #Locs | 5 | 1 | 1 | |
| XB38E06 | 94B13 | #Reps | 9 | 3 | 3 | |
| XB38E06 | 94B13 | #Years | 1 | 1 | 1 | |
| XB38E06 | 94B13 | Diff | 0.2 | 0.3 | 0.7 | |
| XB38E06 | 94B13 | SE Diff | 0.27 | | | |
| XB38E06 | 94B13 | Prob | 0.431 | | | |
| XB38E06 | 93M81 | Mean1 | 8.2 | 5.3 | 6.7 | |

TABLE 2-continued

VARIETY COMPARISON DATA

| Variety1 | Variety2 | Statistic | | | |
|---|---|---|---|---|---|
| XB38E06 | 93M81 | Mean2 | 6.4 | 5.3 | 7.3 |
| XB38E06 | 93M81 | #Locs | 5 | 1 | 1 |
| XB38E06 | 93M81 | #Reps | 9 | 3 | 3 |
| XB38E06 | 93M81 | #Years | 1 | 1 | 1 |
| XB38E06 | 93M81 | Diff | 1.8 | 0 | 0.7 |
| XB38E06 | 93M81 | SE Diff | 0.36 | | |
| XB38E06 | 93M81 | Prob | 0.0068 | | |
| XB38E06 | 93M82 | Mean1 | 8.2 | 5.3 | 6.7 |
| XB38E06 | 93M82 | Mean2 | 7.6 | 5.3 | 6.7 |
| XB38E06 | 93M82 | #Locs | 5 | 1 | 1 |
| XB38E06 | 93M82 | #Reps | 9 | 3 | 3 |
| XB38E06 | 93M82 | #Years | 1 | 1 | 1 |
| XB38E06 | 93M82 | Diff | 0.6 | 0 | 0 |
| XB38E06 | 93M82 | SE Diff | 0.62 | | |
| XB38E06 | 93M82 | Prob | 0.3648 | | |

| Variety1 | Variety2 | Statistic | OILPCT pct ABS | PROTN pct ABS | SPLB count ABS | BSRLF score ABS |
|---|---|---|---|---|---|---|
| XB38E06 | 93B68 | Mean1 | 20.05 | 33.57 | 3037 | |
| XB38E06 | 93B68 | Mean2 | 20.19 | 35.14 | 3046 | |
| XB38E06 | 93B68 | #Locs | 5 | 5 | 6 | |
| XB38E06 | 93B68 | #Reps | 6 | 6 | 9 | |
| XB38E06 | 93B68 | #Years | 1 | 1 | 1 | |
| XB38E06 | 93B68 | Diff | 0.14 | 1.57 | 9 | |
| XB38E06 | 93B68 | SE Diff | 0.139 | 0.31 | 86.1 | |
| XB38E06 | 93B68 | Prob | 0.3652 | 0.0072 | 0.9196 | |
| XB38E06 | 93B85 | Mean1 | 19.44 | 33.97 | 3037 | 9 |
| XB38E06 | 93B85 | Mean2 | 19.89 | 33.6 | 3252 | 6 |
| XB38E06 | 93B85 | #Locs | 9 | 9 | 6 | 1 |
| XB38E06 | 93B85 | #Reps | 10 | 10 | 9 | 1 |
| XB38E06 | 93B85 | #Years | 2 | 2 | 1 | 1 |
| XB38E06 | 93B85 | Diff | 0.45 | 0.37 | 215 | 0 |
| XB38E06 | 93B85 | SE Diff | 0.122 | 0.255 | 33.6 | |
| XB38E06 | 93B85 | Prob | 0.0064 | 0.1862 | 0.0014 | |
| XB38E06 | 93M51 | Mean1 | 19.44 | 33.97 | 3037 | 9 |
| XB38E06 | 93M51 | Mean2 | 19.37 | 33.99 | 2826 | 9 |
| XB38E06 | 93M51 | #Locs | 9 | 9 | 6 | 1 |
| XB38E06 | 93M51 | #Reps | 10 | 10 | 9 | 1 |
| XB38E06 | 93M51 | #Years | 2 | 2 | 1 | 1 |
| XB38E06 | 93M51 | Diff | 0.07 | 0.03 | 211 | 0 |
| XB38E06 | 93M51 | SE Diff | 0.125 | 0.219 | 69.6 | |
| XB38E06 | 93M51 | Prob | 0.5788 | 0.9033 | 0.029 | |
| XB38E06 | 93M80 | Mean1 | 19.44 | 33.97 | 3037 | 9 |
| XB38E06 | 93M80 | Mean2 | 19.36 | 34.37 | 2689 | 9 |
| XB38E06 | 93M80 | #Locs | 9 | 9 | 6 | 1 |
| XB38E06 | 93M80 | #Reps | 10 | 10 | 9 | 1 |
| XB38E06 | 93M80 | #Years | 2 | 2 | 1 | 1 |
| XB38E06 | 93M80 | Diff | 0.08 | 0.4 | 348 | 0 |
| XB38E06 | 93M80 | SE Diff | 0.114 | 0.24 | 40 | |
| XB38E06 | 93M80 | Prob | 0.5156 | 0.1322 | 0.0003 | |
| XB38E06 | 93M90 | Mean1 | 19.44 | 33.97 | 3037 | 9 |
| XB38E06 | 93M90 | Mean2 | 18.9 | 34.71 | 2923 | 9 |
| XB38E06 | 93M90 | #Locs | 9 | 9 | 6 | 1 |
| XB38E06 | 93M90 | #Reps | 10 | 10 | 9 | 1 |
| XB38E06 | 93M90 | #Years | 2 | 2 | 1 | 1 |
| XB38E06 | 93M90 | Diff | 0.54 | 0.74 | 114 | 0 |
| XB38E06 | 93M90 | SE Diff | 0.241 | 0.363 | 89.8 | |
| XB38E06 | 93M90 | Prob | 0.0542 | 0.0753 | 0.2603 | |
| XB38E06 | 93M92 | Mean1 | 20.05 | 33.57 | 3037 | |
| XB38E06 | 93M92 | Mean2 | 19.75 | 34.52 | 2912 | |
| XB38E06 | 93M92 | #Locs | 5 | 5 | 6 | |
| XB38E06 | 93M92 | #Reps | 6 | 6 | 9 | |
| XB38E06 | 93M92 | #Years | 1 | 1 | 1 | |
| XB38E06 | 93M92 | Diff | 0.29 | 0.94 | 125 | |
| XB38E06 | 93M92 | SE Diff | 0.148 | 0.21 | 87.5 | |
| XB38E06 | 93M92 | Prob | 0.1188 | 0.0108 | 0.2132 | |
| XB38E06 | 93M93 | Mean1 | 20.05 | 33.57 | 3037 | |
| XB38E06 | 93M93 | Mean2 | 19.78 | 34.15 | 2847 | |
| XB38E06 | 93M93 | #Locs | 5 | 5 | 6 | |
| XB38E06 | 93M93 | #Reps | 6 | 6 | 9 | |
| XB38E06 | 93M93 | #Years | 1 | 1 | 1 | |
| XB38E06 | 93M93 | Diff | 0.27 | 0.58 | 190 | |
| XB38E06 | 93M93 | SE Diff | 0.173 | 0.435 | 63.3 | |
| XB38E06 | 93M93 | Prob | 0.1966 | 0.2527 | 0.0298 | |
| XB38E06 | 94B13 | Mean1 | 20.05 | 33.57 | 3037 | |

TABLE 2-continued

VARIETY COMPARISON DATA

| Variety1 | Variety2 | Statistic | | | |
|---|---|---|---|---|---|
| XB38E06 | 94B13 | Mean2 | 19.23 | 33.77 | 3165 |
| XB38E06 | 94B13 | #Locs | 5 | 5 | 6 |
| XB38E06 | 94B13 | #Reps | 6 | 6 | 9 |
| XB38E06 | 94B13 | #Years | 1 | 1 | 1 |
| XB38E06 | 94B13 | Diff | 0.81 | 0.2 | 128 |
| XB38E06 | 94B13 | SE Diff | 0.185 | 0.214 | 49.5 |
| XB38E06 | 94B13 | Prob | 0.0117 | 0.4131 | 0.0491 |
| XB38E06 | 93M81 | Mean1 | 20.05 | 33.57 | 3037 |
| XB38E06 | 93M81 | Mean2 | 20.24 | 33.35 | 3031 |
| XB38E06 | 93M81 | #Locs | 5 | 5 | 6 |
| XB38E06 | 93M81 | #Reps | 6 | 6 | 9 |
| XB38E06 | 93M81 | #Years | 1 | 1 | 1 |
| XB38E06 | 93M81 | Diff | 0.19 | 0.22 | 6 |
| XB38E06 | 93M81 | SE Diff | 0.078 | 0.3 | 100.4 |
| XB38E06 | 93M81 | Prob | 0.0678 | 0.5011 | 0.9517 |
| XB38E06 | 93M82 | Mean1 | 20.05 | 33.57 | 3037 |
| XB38E06 | 93M82 | Mean2 | 19.55 | 34.48 | 3085 |
| XB38E06 | 93M82 | #Locs | 5 | 5 | 6 |
| XB38E06 | 93M82 | #Reps | 6 | 6 | 9 |
| XB38E06 | 93M82 | #Years | 1 | 1 | 1 |
| XB38E06 | 93M82 | Diff | 0.5 | 0.91 | 48 |
| XB38E06 | 93M82 | SE Diff | 0.208 | 0.34 | 62.1 |
| XB38E06 | 93M82 | Prob | 0.0752 | 0.056 | 0.4784 |

| Variety1 | Variety2 | Statistic | R160 pct ABS | R180 pct ABS | R181 pct ABS | R182 pct ABS | R183 pct ABS |
|---|---|---|---|---|---|---|---|
| XB38E06 | 93B85 | Mean1 | 9.5 | 4.2 | 27.1 | 51.9 | 7.3 |
| XB38E06 | 93B85 | Mean2 | 9.8 | 4.6 | 28.2 | 49.7 | 7.6 |
| XB38E06 | 93B85 | #Locs | 4 | 4 | 4 | 4 | 4 |
| XB38E06 | 93B85 | #Reps | 4 | 4 | 4 | 4 | 4 |
| XB38E06 | 93B85 | #Years | 1 | 1 | 1 | 1 | 1 |
| XB38E06 | 93B85 | Diff | 0.3 | 0.4 | 1.1 | 2.2 | 0.3 |
| XB38E06 | 93B85 | SE Diff | 0.12 | 0.22 | 1.91 | 1.69 | 0.49 |
| XB38E06 | 93B85 | Prob | 0.1024 | 0.1887 | 0.6 | 0.29 | 0.53 |
| XB38E06 | 93M51 | Mean1 | 9.5 | 4.2 | 27.1 | 51.9 | 7.3 |
| XB38E06 | 93M51 | Mean2 | 10.9 | 4.5 | 24 | 52.2 | 8.4 |
| XB38E06 | 93M51 | #Locs | 4 | 4 | 4 | 4 | 4 |
| XB38E06 | 93M51 | #Reps | 4 | 4 | 4 | 4 | 4 |
| XB38E06 | 93M51 | #Years | 1 | 1 | 1 | 1 | 1 |
| XB38E06 | 93M51 | Diff | 1.4 | 0.3 | 3.1 | 0.3 | 1.2 |
| XB38E06 | 93M51 | SE Diff | 0.54 | 0.23 | 1.73 | 0.96 | 0.74 |
| XB38E06 | 93M51 | Prob | 0.0764 | 0.3615 | 0.17 | 0.78 | 0.22 |
| XB38E06 | 93M80 | Mean1 | 9.5 | 4.2 | 27.1 | 51.9 | 7.3 |
| XB38E06 | 93M80 | Mean2 | 10.7 | 4.7 | 28.3 | 48.9 | 7.3 |
| XB38E06 | 93M80 | #Locs | 4 | 4 | 4 | 4 | 4 |
| XB38E06 | 93M80 | #Reps | 4 | 4 | 4 | 4 | 4 |
| XB38E06 | 93M80 | #Years | 1 | 1 | 1 | 1 | 1 |
| XB38E06 | 93M80 | Diff | 1.2 | 0.5 | 1.1 | 3 | 0.1 |
| XB38E06 | 93M80 | SE Diff | 0.1 | 0.23 | 1.48 | 1.28 | 0.33 |
| XB38E06 | 93M80 | Prob | 0.0013 | 0.1228 | 0.49 | 0.1 | 0.83 |
| XB38E06 | 93M90 | Mean1 | 9.5 | 4.2 | 27.1 | 51.9 | 7.3 |
| XB38E06 | 93M90 | Mean2 | 10.5 | 4.6 | 24 | 52.5 | 8.3 |
| XB38E06 | 93M90 | #Locs | 4 | 4 | 4 | 4 | 4 |
| XB38E06 | 93M90 | #Reps | 4 | 4 | 4 | 4 | 4 |
| XB38E06 | 93M90 | #Years | 1 | 1 | 1 | 1 | 1 |
| XB38E06 | 93M90 | Diff | 1 | 0.4 | 3.1 | 0.6 | 1.1 |
| XB38E06 | 93M90 | SE Diff | 0.24 | 0.31 | 1.53 | 1.73 | 0.4 |
| XB38E06 | 93M90 | Prob | 0.0234 | 0.2919 | 0.13 | 0.75 | 0.07 |

TABLE 3

Soybean SSR Marker Set

SAC1006
SAC1611
SAC1634
SAC1677
SAC1699
SAC1701
SAC1724
SAT_084
SAT_090
SAT_104
SAT_117
SAT_142-DB
SAT_189
SAT_222-DB
SAT_261
SAT_270

TABLE 3-continued

Soybean SSR Marker Set

| | |
|---|---|
| SAT_271-DB | SATT263 |
| SAT_273-DB | SATT264 |
| SAT_275-DB | SATT265 |
| SAT_299 | SATT266 |
| SAT_301 | SATT267 |
| SAT_311-DB | SATT270 |
| SAT_317 | SATT272 |
| SAT_319-DB | SATT274 |
| SAT_330-DB | SATT279 |
| SAT_331-DB | SATT280 |
| SAT_343 | SATT282 |
| SAT_351 | SATT284 |
| SAT_366 | SATT285 |
| SAT_381 | SATT287 |
| SATT040 | SATT292 |
| SATT042 | SATT295 |
| SATT050 | SATT299 |
| SATT092 | SATT300 |
| SATT102 | SATT307 |
| SATT108 | SATT314 |
| SATT109 | SATT319 |
| SATT111 | SATT321 |
| SATT115 | SATT322 |
| SATT122 | SATT326 |
| SATT127 | SATT327 |
| SATT129 | SATT328 |
| SATT130 | SATT330 |
| SATT131 | SATT331 |
| SATT133 | SATT332 |
| SATT142 | SATT333 |
| SATT144 | SATT334 |
| SATT146 | SATT335 |
| SATT147 | SATT336 |
| SATT150 | SATT338 |
| SATT151 | SATT339 |
| SATT153 | SATT343 |
| SATT155 | SATT346 |
| SATT156 | SATT347 |
| SATT165 | SATT348 |
| SATT166 | SATT352 |
| SATT168 | SATT353 |
| SATT172 | SATT355 |
| SATT175 | SATT356 |
| SATT181 | SATT357 |
| SATT183 | SATT358 |
| SATT186 | SATT359 |
| SATT190 | SATT361 |
| SATT191 | SATT364 |
| SATT193 | SATT367 |
| SATT195 | SATT369 |
| SATT196 | SATT373 |
| SATT197 | SATT378 |
| SATT199 | SATT380 |
| SATT202 | SATT383 |
| SATT203 | SATT385 |
| SATT204 | SATT387 |
| SATT212 | SATT389 |
| SATT213 | SATT390 |
| SATT216 | SATT391 |
| SATT219 | SATT393 |
| SATT221 | SATT398 |
| SATT225 | SATT399 |
| SATT227 | SATT406 |
| SATT228 | SATT409 |
| SATT230 | SATT411 |
| SATT233 | SATT412 |
| SATT243 | SATT413 |
| SATT247 | SATT414 |
| SATT249 | SATT415 |
| SATT250 | SATT417 |
| SATT251 | SATT418 |
| SATT255 | SATT420 |
| SATT256 | SATT421 |
| SATT257 | SATT422 |
| SATT258 | SATT423 |
| SATT259 | SATT429 |
| SATT262 | SATT431 |

TABLE 3-continued

Soybean SSR Marker Set

SATT432
SATT433
SATT436
SATT440
SATT441
SATT442
SATT444
SATT448
SATT451
SATT452
SATT454
SATT455
SATT457
SATT460
SATT461
SATT464
SATT466
SATT467
SATT469
SATT470
SATT471
SATT473
SATT475
SATT476
SATT477
SATT478
SATT479
SATT480
SATT487
SATT488
SATT491
SATT492
SATT493
SATT495
SATT497
SATT503
SATT508
SATT509
SATT510
SATT511
SATT512
SATT513
SATT514
SATT515
SATT517
SATT519
SATT522
SATT523
SATT524
SATT526
SATT529
SATT533
SATT534
SATT536
SATT537
SATT540
SATT544
SATT545
SATT546
SATT548
SATT549
SATT550
SATT551
SATT552
SATT555
SATT556
SATT557
SATT558
SATT565
SATT566
SATT567
SATT568
SATT569
SATT570
SATT572
SATT573
SATT576

TABLE 3-continued

Soybean SSR Marker Set

SATT578
SATT583
SATT584
SATT586
SATT587
SATT590
SATT591
SATT594
SATT595
SATT596
SATT597
SATT598
SATT601
SATT602
SATT608
SATT613
SATT614
SATT617
SATT618
SATT628
SATT629
SATT630
SATT631
SATT632-TB
SATT633
SATT634
SATT636
SATT640-TB
SATT651
SATT654
SATT655-TB
SATT656
SATT660
SATT661-TB
SATT662
SATT665
SATT666
SATT667
SATT672
SATT675
SATT677
SATT678
SATT680
SATT701
SATT708-TB
SATT712
SATT234
SATT240
SATT242
SATT507
SATT581
SATT684
SATT506
SATT582
SATT685

All publications, patents and patent applications mentioned in the specification are indicative of the level of those skilled in the art to which this invention pertains. All such publications, patents and patent applications are incorporated by reference herein for the purpose cited to the same extent as if each was specifically and individually indicated to be incorporated by reference herein.

The foregoing invention has been described in detail by way of illustration and example for purposes of clarity and understanding. As is readily apparent to one skilled in the art, the foregoing are only some of the methods and compositions that illustrate the embodiments of the foregoing invention. It will be apparent to those of ordinary skill in the art that variations, changes, modifications and alterations may be applied to the compositions and/or methods described herein without departing from the true spirit, concept and scope of the invention.

What is claimed is:

1. A seed of soybean variety XB38E06, representative seed of said soybean variety XB38E06 having been deposited under ATCC Accession Number PTA-7743.

2. A soybean plant, or a part thereof, produced by growing the seed of claim 1.

3. The soybean plant, or a part thereof, of claim 2 wherein said part is pollen.

4. The soybean plant, or a part thereof, of claim 2 wherein said part is an ovule.

5. A soybean plant, or a part thereof, expressing all the physiological and morphological characteristics of soybean variety XB38E06, representative seed of said soybean variety having been deposited under ATCC Accession Number PTA-7743.

6. A tissue culture produced from protoplasts or regenerable cells from the plant of claim 2.

7. The tissue culture according to claim 6, wherein the cells or protoplasts are produced from a plant tissue selected from the group consisting of: leaf, pollen, cotyledon, hypocotyl, embryos, root, pod, flower, shoot and stem.

8. A soybean plant regenerated from the tissue culture of claim 6 having all the morphological and physiological characteristics of soybean variety XB38E06, representative seed of said soybean variety XB38E06 having been deposited under ATCC Accession Number PTA-7743.

9. A method for producing a soybean seed comprising crossing two soybean plants and harvesting the resultant soybean seed, wherein at least one soybean plant is the soybean plant of claim 2.

10. A method for producing hybrid soybean seed comprising crossing the soybean plant according to claim 2 with a second soybean plant and harvesting the resultant hybrid soybean seed.

11. A method for producing a XB38E06 derived soybean plant, comprising:

a. Crossing soybean variety XB38E06, a sample of said soybean variety deposited under ATCC Accession Number PTA-7743, with a second soybean plant to yield progeny soybean seed; and b. Growing said progeny soybean seed to yield said XB38E06-derived soybean plant.

12. The method of claim 11, wherein the second soybean plant is transgenic.

13. A method of producing a herbicide resistant soybean plant comprising introducing a transgene conferring herbicide resistance into the plant of claim 2.

14. A herbicide resistant soybean plant produced by the method of claim 13.

15. The soybean plant of claim 14, wherein the transgene confers resistance to a herbicide selected from the group consisting of glyphosate, sulfonylurea, imidazolinone, glufosinate, phenoxy proprionic acid, cycloshexone, triazine, and benzonitrile.

16. A method of producing a pest or insect resistant soybean plant comprising introducing a transgene conferring pest or insect resistance into the soybean plant of claim 2.

17. A pest or insect resistant soybean plant produced by the method of claim 16.

18. The soybean plant of claim 17, wherein the transgene encodes a *Bacillus thuringiensis* (Bt) endotoxin.

19. A method of producing a disease resistant soybean plant comprising introducing a transgene into the soybean plant of claim 2.

20. A disease resistant soybean plant produced by the method of claim 19.

* * * * *